(12) United States Patent
Achyuta et al.

(10) Patent No.: US 9,662,229 B2
(45) Date of Patent: May 30, 2017

(54) ARRAY OF MICROELECTRODES FOR INTERFACING TO NEURONS WITHIN FASCICLES

(71) Applicant: The Charles Stark Draper Laboratory, Inc., Cambridge, MA (US)

(72) Inventors: Anilkumar H. Achyuta, Cambridge, MA (US); Bryan McLaughlin, Cambridge, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 15/296,738

(22) Filed: Oct. 18, 2016

(65) Prior Publication Data

US 2017/0035582 A1    Feb. 9, 2017

Related U.S. Application Data

(62) Division of application No. 14/615,689, filed on Feb. 6, 2015.

(Continued)

(51) Int. Cl.
*A61N 1/00* (2006.01)
*A61F 2/50* (2006.01)
*A61F 2/72* (2006.01)

(52) U.S. Cl.
CPC .............. *A61F 2/5044* (2013.01); *A61F 2/72* (2013.01)

(58) Field of Classification Search
CPC ....... A61F 2/5044; A61F 2/72; A61N 1/0551; A61N 1/0556; A61N 1/0558; A61B 5/6877; A61B 5/04001
See application file for complete search history.

(56) References Cited

U.S. PATENT DOCUMENTS

| 4,969,468 A | 11/1990 | Byers et al. ................. 128/642 |
| 5,215,088 A | 6/1993 | Normann et al. ............ 128/642 |

(Continued)

FOREIGN PATENT DOCUMENTS

| EP | 2 197 504 B1 | 8/2011 | ............. A61L 27/24 |
| WO | WO 2006/042287 A2 | 4/2006 | ............... C12N 5/06 |

(Continued)

OTHER PUBLICATIONS

Blackrock Microsystems, Microelectrode Arrays, 2 pages.

(Continued)

*Primary Examiner* — Mallika D Fairchild
(74) *Attorney, Agent, or Firm* — Sunstein Kann Murphy & Timbers LLP

(57) ABSTRACT

Methods and apparatus are disclosed for interfacing with nerve fibers, such as axons. Embodiments provide multiple micro-channels, into which individual fascicles of a nerve may be placed, one fascicle per micro-channel. Each micro-channel has an associated set of micro-wire electrodes that penetrate the fascicle in the micro-channel. The micro-wire electrodes are thinner than prior art photolithographed micro-electrode arrays. Consequently, more micro-wire electrodes may interface with a single fascicle, and each micro-wire electrode interfaces with fewer axons, than in the prior art. Multiple rows of micro-channels may be stacked to construct two-dimensional arrays of micro-channels. These embodiments thereby facilitate finer motor control in prosthetic devices, and more granular sensory feedback from prosthetic devices to central nervous systems, than is achievable in the prior art.

12 Claims, 20 Drawing Sheets

Related U.S. Application Data

(60) Provisional application No. 61/936,541, filed on Feb. 6, 2014.

(56) References Cited

U.S. PATENT DOCUMENTS

| | | | |
|---|---|---|---|
| 5,361,760 A | 11/1994 | Normann et al. | 128/642 |
| 6,060,336 A * | 5/2000 | Wan | B81C 1/0019 216/2 |
| 6,456,866 B1 | 9/2002 | Tyler et al. | 600/377 |
| 7,951,300 B2 | 5/2011 | Bhandari et al. | 216/11 |
| 7,991,475 B1 | 8/2011 | Tang et al. | 607/45 |
| 8,226,661 B2 | 7/2012 | Balling et al. | 606/129 |
| 8,359,083 B2 | 1/2013 | Clark et al. | 600/378 |
| 2007/0142889 A1 | 6/2007 | Whitehurst et al. | 607/118 |
| 2007/0260170 A1 | 11/2007 | Levin et al. | 604/20 |
| 2008/0138581 A1 | 6/2008 | Bhandari et al. | 428/156 |
| 2008/0228240 A1* | 9/2008 | Edell | A61B 5/04888 607/48 |
| 2008/0300691 A1 | 12/2008 | Romero-Ortega et al. | 623/23.72 |
| 2009/0004471 A1 | 1/2009 | Amthor | 428/375 |
| 2010/0152699 A1 | 6/2010 | Ferrari et al. | 604/500 |
| 2010/0285972 A1* | 11/2010 | Dubrow | B01J 20/28007 506/7 |
| 2011/0021943 A1 | 1/2011 | Lacour et al. | 600/546 |
| 2011/0250585 A1 | 10/2011 | Ingber et al. | 435/5 |
| 2013/0134546 A1* | 5/2013 | Cheng | A61B 5/04001 257/506 |
| 2014/0228738 A1 | 8/2014 | Park et al. | 604/20 |
| 2014/0234157 A1* | 8/2014 | Chen | H01B 1/02 420/507 |

FOREIGN PATENT DOCUMENTS

| | | | | |
|---|---|---|---|---|
| WO | WO 2009/030901 A2 | 3/2009 | | A61L 27/24 |
| WO | WO 2011/044116 A2 | 4/2011 | | C12M 3/00 |
| WO | WO 2012/139124 A1 | 10/2012 | | A61B 5/05 |
| WO | WO 2013/011474 A2 | 1/2013 | | A61N 1/32 |
| WO | WO 2013/111985 A1 | 8/2013 | | A61N 1/04 |

OTHER PUBLICATIONS

Cipriani, et al., "A Novel Concept for a Prosthetic Hand With a Bidirectional Interface: A Feasibility Study," Biomedical Engineering, IEEE, vol. 56, issue 11, pp. 2739-2743, Sep. 2009.
Di Pino, et al., "Neuroplasticity in amputees: main implications on bidirectional interfacing of cybernetic hand prostheses," Prog Neurobiol., vol. 88, issue 2, pp. 114-126, Jun. 2009, Abstract.
EurekAlert!, "The quest for a better bionic hand," http://www.eurekalert.org/pub_releases/2013-02/epfd-tqf021113.php, Feb. 2013, 2 pages.
Garde, et al., "Early interfaced neural activity from chronic amputed nerves," Frontiers in Neuroengineering, vol. 2, article 5, May 2009, 11 pages.
Ikeuchi, et al., "Membrane Micro Emboss (MeME) Process for 3-D Membrane Microdevice," Micro Electronics and Mechanical Systems, Dec. 2009, 15 pages.
International Searching Authority, International Search Report—International Application No. PCT/US2015/014741, dated Apr. 28, 2015, together with the Written Opinion of the International Searching Authority, 13 pages.
Kozai, et al., "Ultrasmall implantable composite microelectrodes with bioactive surfaces for chronic neural interfaces," Nature Materials, vol. 11, pp. 1065-1073, Dec. 2012, 9 pages.
Lehew, et al., "Chapter 1: State-of-the-Art Microwire Array Design for Chronic Neural Recordings in Behaving Animals," NCBI Bookshelf, Methods for Neural Ensemble Recordings, $2^{nd}$ Edition, 2008. 29 pages.
Lotfi, et al., Modality-specific axonal regeneration: toward selective regenerative neural interfaces, Frontiers in Neuroengineering, vol. 4, article 11, Oct. 2011, 11 pages.
Minev, et al., "High sensitivity recording of afferent nerve activity using ultra-compliant microchannel electrodes: an acute in vivo validation," J. Neural Eng., vol. 9, issue 2, Apr. 2012, 1 page, Abstract.
Plexon, Microwire Array, http://www.plexon.com/products/microwire-array, Apr. 2012, 2 pages.
Plexon, Microwire Array, http://www.plexon.com/products/microwire-array, Mar. 2013, 1 page.
Plexon, Microwire Array, http://www.plexon.com/products/microwire-array, Mar. 2013, 2 pages.
Plexon, Plexon Electrodes Data Sheet, Mar. 9, 2013, 2 pages.
Srinivasan, et al., "Regenerative Microchannel Electrode Array for Peripheral Nerve interfacing", Proceedings of the $5^{th}$ International IEEE EMBS Conference on Neural Engineering, Apr./May 2011, 4 pages.
Tucker-Davis Technologies, Microwire Arrays, http://www.tdt.com/products/MW16.htm, Jul. 2012, 4 pages.
United States Patent and Trademark Office, Non-Final Office Action, U.S. Appl. No. 14/615,689, 26 pages, Sep. 18, 2015.
United States Patent and Trademark Office, Final Office Action, U.S. Appl. No. 14/615,689, 16 pages, Jun. 23, 2016.
University of Twente, Reflex leg: Control of leg prostheses through biodirectional information exchange with the body, 2 pages.
Wieringa, et al. "Neural Growth Into A Microchannel Network: Towards a Regenerative Neural Interface," Proceedings of the $4^{th}$ International IEEE EMBS Conference on Neural Engineering, Apr./May 2009, 5 pages.
Wikipedia, Electrospinning, http://en.wikipedia.org/wiki/Electrospinning , Aug. 2013, 6 pages.
Wikipedia, Immunotherapy, http://en.wikipedia.org/wiki/Immunomodulation Jul. 2013, 11 pages.
Wikipedia, Neuroregeneration, http:en/wikipedia.org/wiki/Neuroregeneration, May 2013, 8 pages.

* cited by examiner

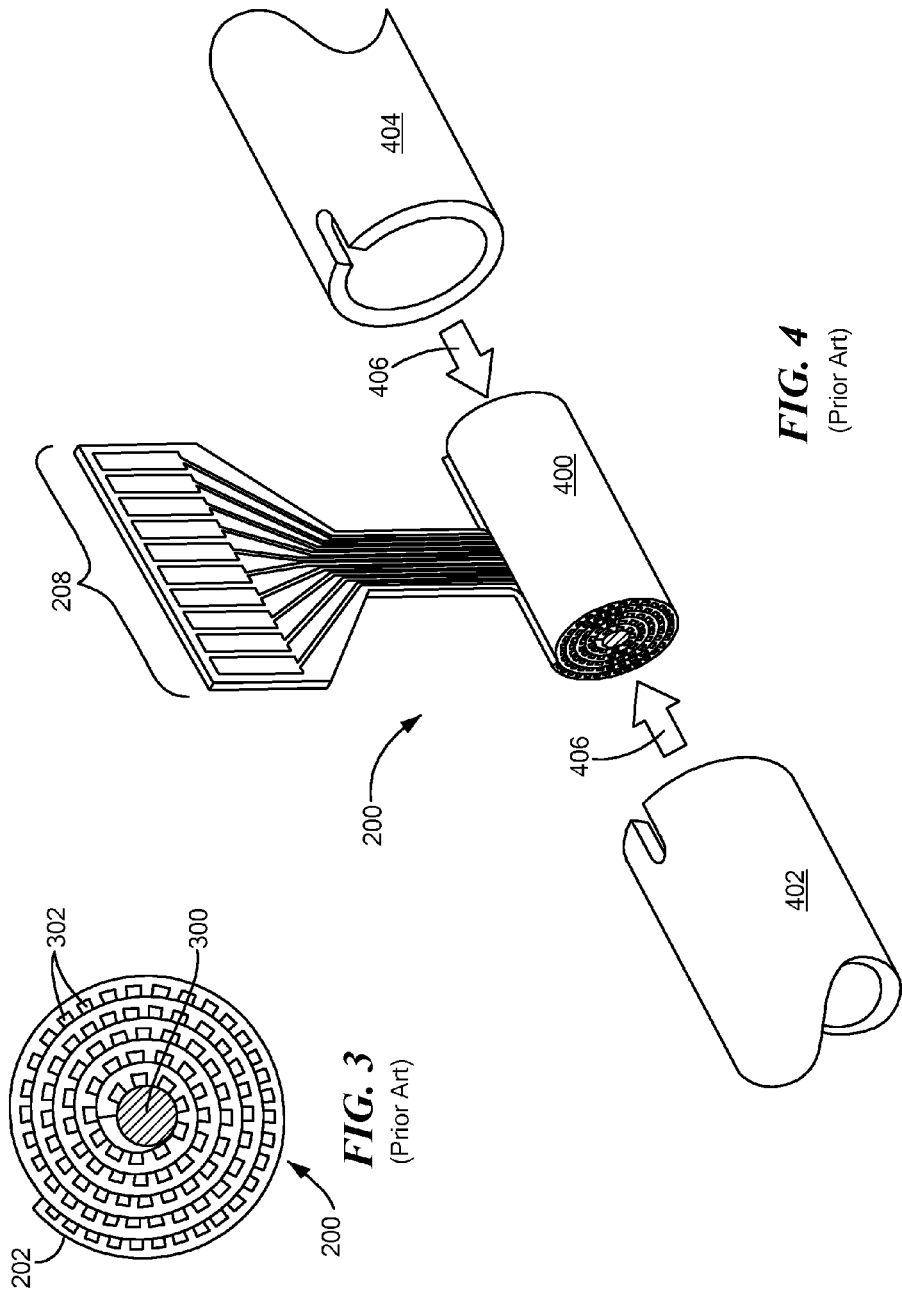

ARRAY OF MICROELECTRODES FOR INTERFACING TO NEURONS WITHIN FASCICLES

CROSS REFERENCE TO RELATED APPLICATIONS

This application is a divisional of U.S. patent application Ser. No. 14/615,689, filed Feb. 6, 2015, and titled "Array of Microelectrodes for Interfacing to Neurons within Fascicles," which claims the benefit of U.S. Provisional Patent Application No. 61/936,541, filed Feb. 6, 2014, and titled "Array of Microelectrodes for Interfacing to Neurons within Fascicles," the entire contents of each of which are hereby incorporated by reference herein, for all purposes.

TECHNICAL FIELD

The present invention relates to nerve electrode arrays and, more particularly, to nerve electrode arrays that define micro-channels, each micro-channel including a plurality of micro-wire electrodes.

BACKGROUND ART

Limb amputations can significantly negatively impact amputees' lives. Fortunately, prosthetic devices can partially compensate for loss of limb structure (bone, skin, etc.) and actuation (muscle). An ideal, albeit not yet developed, prosthetic device would include a separate motor for each lost muscle or degree of limb freedom, and each such motor would be driven by a discrete signal from the amputee's nervous system. Similarly, the ideal prosthetic device would include a sensor (touch, temperature, etc.) corresponding to each sense signal the amputated limb would otherwise have sent to the amputee's nervous system.

In a nervous system, efferent axons, otherwise known as motor or effector neurons, carry nerve impulses from a central nervous system to effectors, such as muscles and glands. On the other hand, afferent axons, otherwise known as sensory nerves or receptor neurons, carry nerve impulses from receptors or sense organs towards the central nervous system. Neural interfaces are, therefore, important for coupling efferent and afferent nerves to motors and sensors, respectively, in prosthetic devices.

Interfacing with efferent and afferent axons is difficult, at least in part due to their small sizes. In general, as illustrated in FIG. 1, a peripheral nerve 100 includes blood vessels 102 and several fascicles 104, each fascicle containing a bundle of axons 106. A typical mammalian fascicle is about 500 μm in diameter, but the diameter may vary depending on location and function of the nerve fiber. Fascicles in other animals may be other sizes.

In some prior art nerve interfaces, three electrodes are disposed longitudinally along a nerve or a fascicle. Two of the electrodes are used to establish an electrical reference voltage, and the third electrode provides an electrical measurement signal. However, the electrical measurement provides an integrated signal, i.e., a sum of signals from a plurality of axons in the nerve or fascicle. A fascicle contains a combination of efferent and afferent axons, and all the efferent axons typically do not control a single muscle. Thus, the integrated measurement signal is of limited value for selectively driving a motor of a prosthetic device.

Higher density neural interfaces, i.e., interfaces that provide an electrical signal from a small numbers of axons, ideally from one axon, would facilitate finer motor control in prosthetic devices than is achievable in the prior art. Similarly, higher density neural interfaces would facilitate more granular sensory feedback from prosthetic devices to central nervous systems.

SUMMARY OF EMBODIMENTS

Embodiments of the present invention facilitate finer motor control in prosthetic devices, and more granular sensory feedback from prosthetic devices to central nervous systems, than is achievable in the prior art. Some embodiments provide sets of generally trench-shaped micro-channels, into which fascicles of a nerve may be placed, one fascicle per micro-channel. One or more lids may be placed over the micro-channels to close the micro-channels and secure the fascicles in the trenches. Each micro-channel has an associated set of micro-wire electrodes. In some embodiments, the electrodes extend down from the lid(s) into the trenches. In other embodiments, the electrodes extend up from the bottoms of the trenches. In either case, the electrodes penetrate the fascicles and make electrical contact with axons within the fascicles. Several rows of micro-channels may be stacked to create a two-dimensional array of micro-channels.

An embodiment of the present invention provides an electrode array. The electrode array includes a substrate that includes a bio-compatible dielectric and at least one nerve micro-channel. Each nerve micro-channel includes a trench defined by the substrate. The trench is at most about 2.5 cm wide. Each nerve micro-channel also includes a lid associated with the trench. The lid includes a bio-compatible dielectric. The lid is configured to be attachable to the substrate so as to close the trench at least along at least a portion of the trench's length such that, when the lid closes the trench, the substrate and the lid collectively define a respective nerve capture volume within the trench. Each nerve micro-channel also includes at least three micro-wire electrodes. Each micro-wire electrode protrudes from the substrate defining the trench and/or from the lid associated with the trench. Each micro-wire electrode has a diameter of at most about 25 μm substantially along its protrusion.

The trench may be at most about 5,000 μm wide. The trench may be at most about 500 μm wide. The trench may be at most about 20 μm wide.

The at least one nerve micro-channel may include a plurality of horizontally distributed nerve micro-channels.

The at least one nerve micro-channel may include a plurality of vertically distributed rows of nerve micro-channels. Each row of nerve micro-channels includes a plurality of horizontally distributed nerve micro-channels.

For each nerve micro-channel, the at least three micro-wire electrodes may be arranged in a two-dimensional array having a spacing between adjacent micro-wire electrodes less than about 100 μm. The at least three micro-wire electrodes may be arranged in a two-dimensional array having a spacing between adjacent micro-wire electrodes less than about 40 μm. The at least three micro-wire electrodes may be arranged in a two-dimensional array having a spacing between adjacent micro-wire electrodes less than about 20 μm.

For each nerve micro-channel, the at least three micro-wire electrodes may be arranged along at least one diagonal line, relative to a longitudinal axis of the trench.

For each nerve micro-channel, at least one micro-wire electrode of the at least three micro-wire electrodes may protrude at most about 125 μm and less than about 250 μm.

Another at least one micro-wire electrode of the at least three micro-wire electrodes may protrude at least about 275 μm.

For each nerve micro-channel, the at least three micro-wire electrodes may include a plurality of groups of micro-wire electrodes. Each group of micro-wire electrodes may include at least five micro-wire electrodes. Each group of micro-wire electrodes may be spaced longitudinally along the trench, such that micro-wire electrodes of two adjacent groups of micro-wire electrodes are spaced at most about 125 μm apart.

The electrode array may also include, for each nerve micro-channel, a substantially planar electrode in the substrate defining the trench and/or in the lid associated with the trench and electrically exposed to the nerve capture volume within the trench.

Each micro-wire electrode may include an electrically conductive core and an electrically non-conductive layer surrounding the core. The electrically non-conductive layer surrounding the core is substantially along the length of the micro-wire electrode protruding from the substrate defining the trench and/or the lid associated with the trench. The electrically non-conductive layer surrounding the core exposes at most about a 10 μm distal end portion of the core.

The electrically conductive core may include metal, an electrically conductive polymer and/or a carbon fiber.

The electrically non-conductive layer may include glass.

Another embodiment of the present invention provides a method for attaching electrodes to portions of a nerve. The method includes making a longitudinal incision in an epineurial sheath of the nerve, without laterally bisecting the nerve. A portion of at least one fascicle is displaced, through the incision, from inside the epineurial sheath to outside the epineurial sheath, thereby defining a displaced fascicle. At least a portion of the displaced fascicle is disposed in a trench of a nerve micro-channel. The displaced fascicle is penetrated with micro-wire electrodes of the micro-channel. A lid is attached to the micro-channel, thereby enclosing the displaced fascicle in the trench.

Displacing the portion of the at least one fascicle from inside the epineurial sheath to outside the epineurial sheath may include displacing a plurality of fascicles from inside the epineurial sheath to outside the epineurial sheath, thereby defining a plurality of displaced fascicles. Disposing the at least the portion of the displaced fascicle in the trench of a nerve micro-channel may include disposing each fascicle of the plurality of displaced fascicles in a trench of a respective nerve micro-channel of a plurality of micro-channels. Penetrating the displaced fascicle with the micro-wire electrodes of the micro-channel may include penetrating each fascicle of the plurality of displaced fascicles with respective micro-wire electrodes of the respective micro-channel of the plurality of micro-channels. Attaching a lid to the micro-channel includes attaching the lid to the plurality of micro-channels.

BRIEF DESCRIPTION OF THE DRAWINGS

The invention will be more fully understood by referring to the following Detailed Description of Specific Embodiments in conjunction with the Drawings, of which:

FIG. 3 is an end view of the nerve electrode array of FIG. 2, once the electrode array has been rolled upon a mandrel.

FIG. 4 illustrates nerve pieces being attached to the nerve electrode array of FIG. 3.

DETAILED DESCRIPTION OF SPECIFIC EMBODIMENTS

In accordance with embodiments of the present invention, methods and apparatus are disclosed for interfacing with nerve fibers, such as axons. These embodiments provide multiple micro-channels, into which individual fascicles of a nerve may be placed, one fascicle per micro-channel. Each micro-channel has an associated set of micro-wire electrodes that penetrate the fascicle in the micro-channel. The micro-wire electrodes are thinner than prior art photolithographed micro-electrode arrays. Consequently, more micro-wire electrodes may interface with a single fascicle, and each micro-wire electrode interfaces with fewer axons, than in the prior art. These embodiments thereby facilitate finer motor control in prosthetic devices, and more granular sensory feedback from prosthetic devices to central nervous systems, than is achievable in the prior art.

Figure 1:
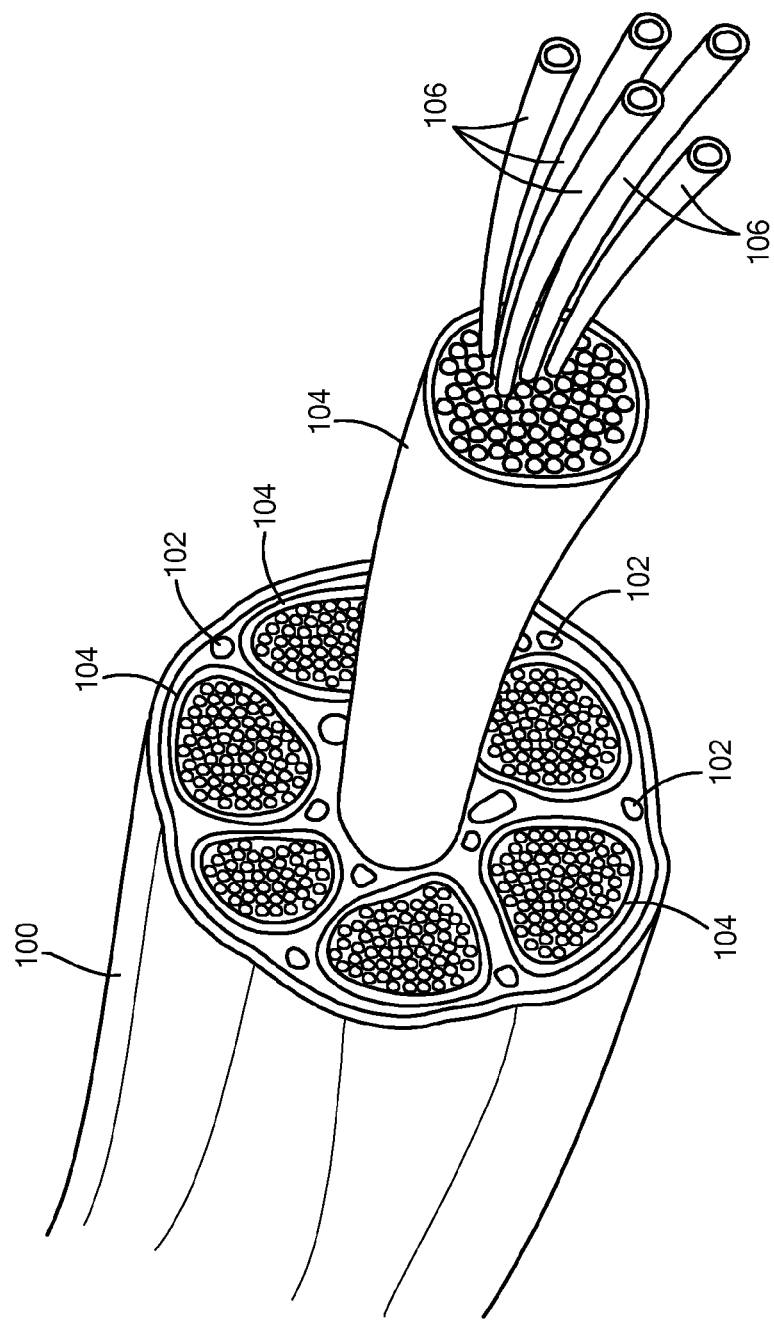
FIG. 1 is a perspective schematic illustration of a peripheral nerve, including fascicles and other items found in the nerve, as is well known in the art.
Figure 2:
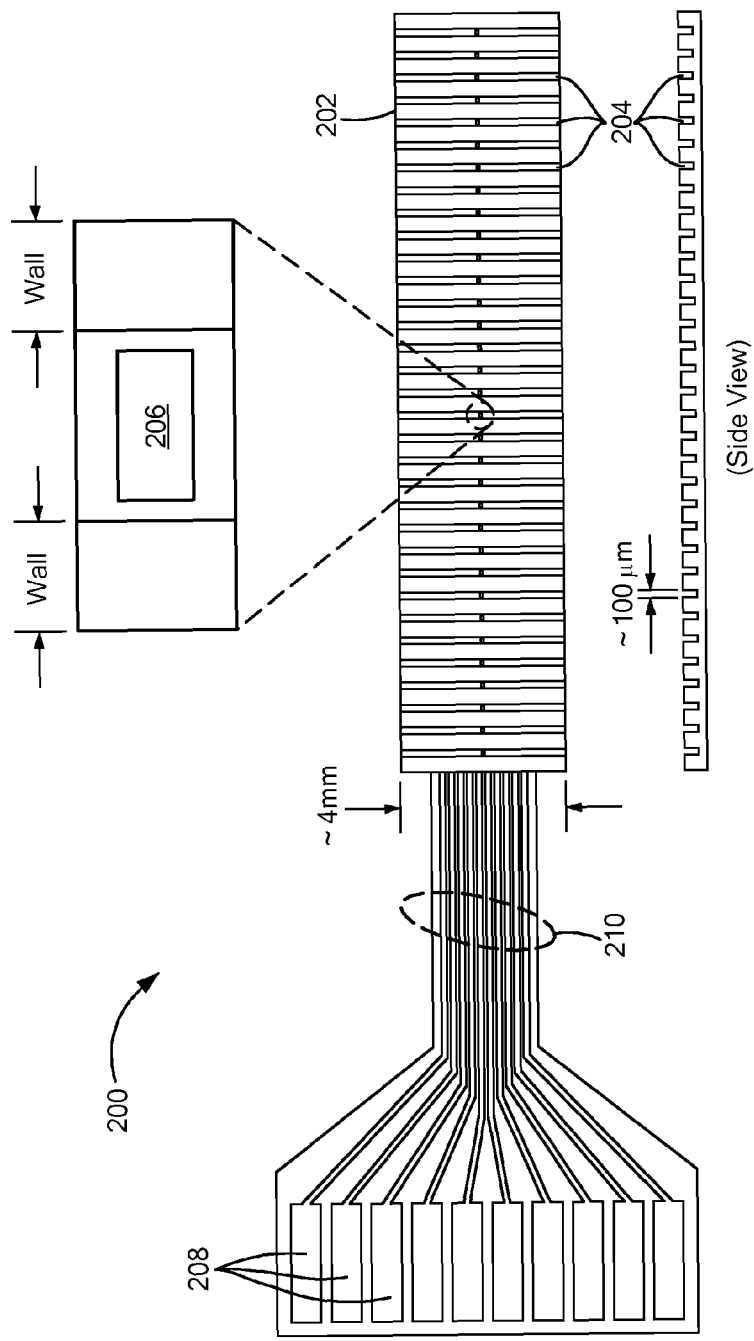
FIG. 2 is a plan view of a "jelly roll" nerve electrode array, according to the prior art.

Some prior art attempts to interface with nerves involve inserting an electrode array between two portions of a severed nerve. The nerve may have been severed as a result of an injury, or the nerve may be severed during surgery for the purpose of inserting the electrode array. FIG. 2 is a plan view of a prior art "jelly roll" nerve electrode array 200, before it is rolled up. The nerve electrode array 200 includes a flexible plate 202 defining a plurality of parallel groves 204, also shown in side view. Each of the groves 204 includes an exposed electrode, as exemplified by electrode 206 in the enlarged portion of the figure. Each electrode 206 is electrically connected to a respective contact pad 208, for connection to an external circuit. As shown schematically in FIG. 3, the flexible plate 202 is rolled around a mandrel 300 to form an approximate cylinder 400, schematically illustrated in FIG. 4. Returning to FIG. 3, adjacent layers of the spiral-wound flexible plate 202 cap the grooves 204 of the layer below to form channels 302 extending longitudinally through the cylinder.

Figure 5:
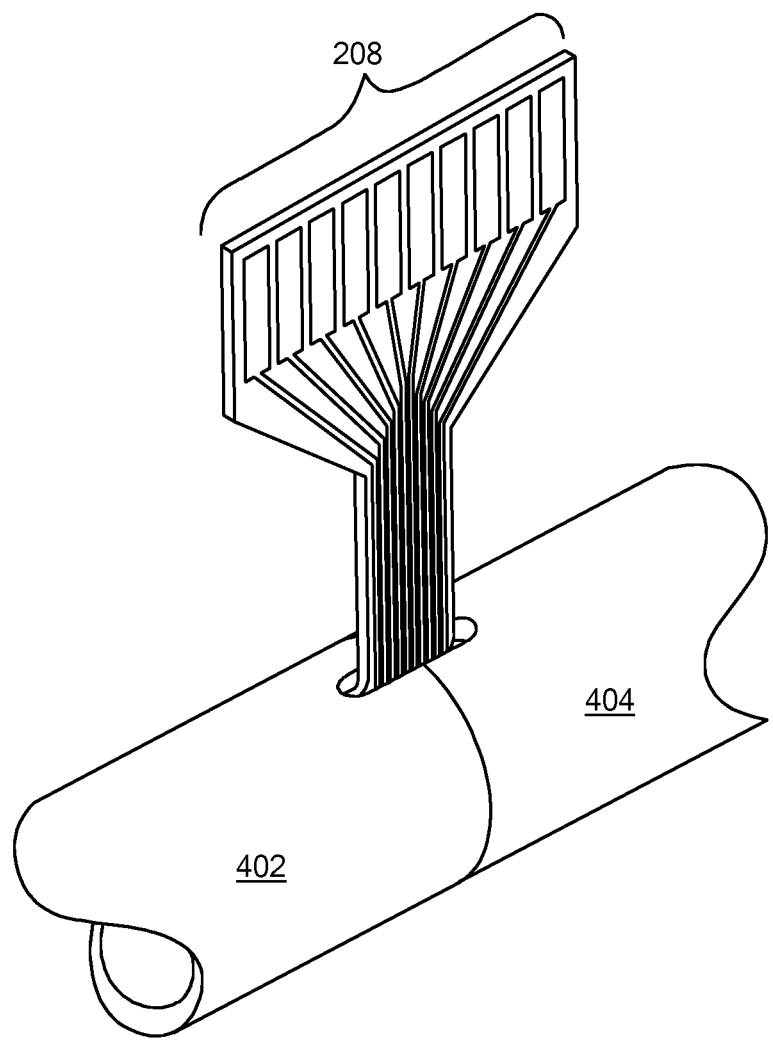
FIG. 5 illustrates the nerve pieces having been attached to the nerve electrode array.

In use, a nerve is severed into two pieces 402 and 404, as shown schematically in FIG. 4. Each piece 402 and 404 of the nerve is butted to, or slightly overlaps, a respective end of the cylinder 400, as indicated by arrows 406, yielding a configuration schematically illustrated in FIG. 5. Theoretically, axons from both of the severed nerve pieces 402 and 404 regenerate through the channels 302 and rejoin within the cylinder 400. Thus, the cylinder provides a scaffold for the axons to regenerate. Once a regenerated axon reaches its corresponding electrode 206 (FIG. 2), theoretically electrical signals from the axon may be detected by a circuit coupled to the contact pads 208.

Problematically, the mandrel 300 (FIG. 3) blocks the central portion (in cross section) of the cylinder 400, thereby preventing axon regeneration through the core of the cylinder. The central portions (in cross section) of the nerve pieces 402 and 404 are typically the most important, in terms of nerve pulse transmission. Therefore, the prior art jelly-roll nerve electrode array 200 blocks, or at least inhibits, regeneration of the most important axons, and it includes no electrodes to interface with these important axons.

In addition, the number of electrodes, and therefore channels, that can be individually electrically connected to an external circuit is limited by density of electrical interconnects 210 (FIG. 2) between the electrodes 206 and the contact pads 208. In a state-of-the-art jelly-roll nerve electrode array, only about 20 electrical connections can be accommodated. To put this number in perspective, a human arm has 22 degrees of freedom. Therefore, at least 22 distinct electrical connections to electrodes and a similar number of distinct channels are needed to drive a fully animated prosthetic arm. If more than one electrode per channel and/or neural feedback to the central nervous system is desired, additional electrical connections are required. In many cases, dozens or hundreds of distinct electrical connections are desired.

Figure 8:
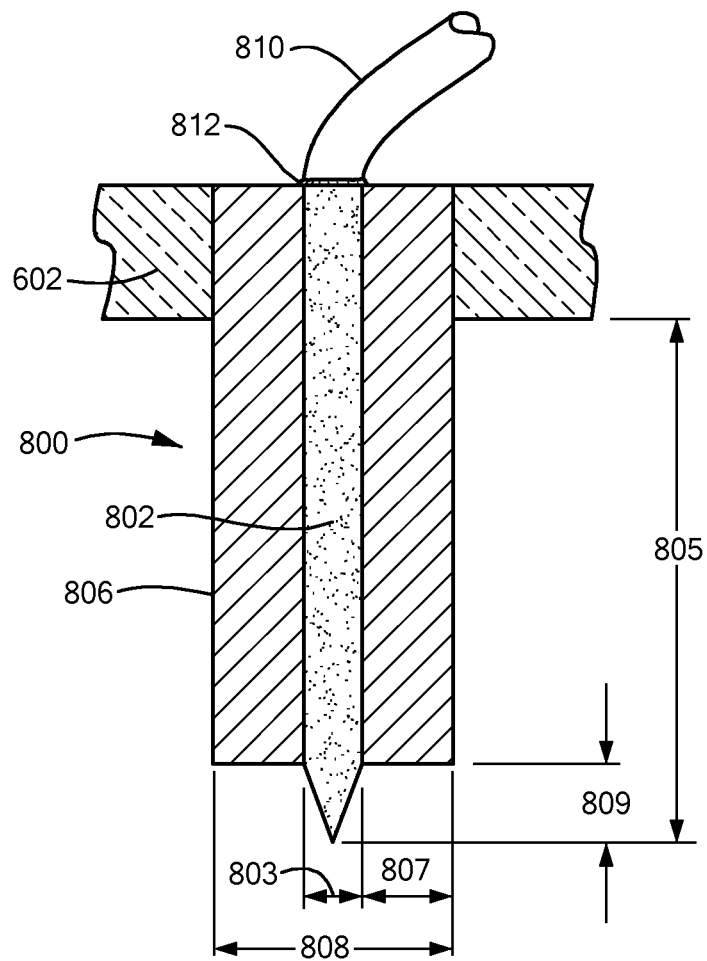
FIG. 8 is a schematic cross-sectional view (enlarged, relative to FIGS. 6 and 7, but not to scale) of a portion of the lid and one micro-wire electrode of FIGS. 6 and 7.

Placing more than one jelly-roll nerve electrode array in parallel to accommodate additional electrical connections creates additional problems, such as mismatches between geometry of the nerve (essentially round) and geometry of the faces of the electrode arrays (figure-8 for two arrays, etc.) Furthermore, if three or more electrode arrays are placed in parallel, gaps are formed among the cylinders 400 of the electrode arrays. These gaps provide no scaffolding or electrodes, yet axons might regenerate through them.

Furthermore, regeneration of the axons through the channels 302 is not specific. That is, any axon, or group of axons, may attempt to regenerate through a given channel 302. Thus, it is difficult or impossible to predict which type of axons, for example efferent or afferent, muscle or glad, etc., will regenerate through a given channel 302 and, therefore, it is difficult or impossible to predict whether electrical signals should be sensed from, or injected into, the channel's electrode 206, or which signals to expect to be associated with the channel's electrode.

If more than one efferent axon regenerates through a single channel 302, the electrical signals available at the corresponding contact pad 208 would be a combination of signals from more than one axon. Worse, if an afferent axon and an efferent axon both regenerate through a single channel 302, electrical stimulation introduced by a circuit through the channel's electrode 206 could cause undesirable side effects.

Embodiments of the present invention overcome these and other shortcomings of the prior art, such as by facilitating interfacing an electrode with a small number of axons, ideally one axon per electrode. As noted, some embodiments provide multiple micro-channels, into which individual fascicles of a nerve may be placed, and micro-electrodes for interfacing with axons within the fascicles. It should be noted that the prior art jelly-roll nerve electrode array is intended to repair a break in a nerve or require the nerve to be surgically severed in order to be connected to the jelly-roll nerve electrode arrays. However, advantageously, fascicles may be place in the disclosed micro-channels and electrically connected to the disclosed electrodes, without severing fascicles or nerves.

Figure 6:
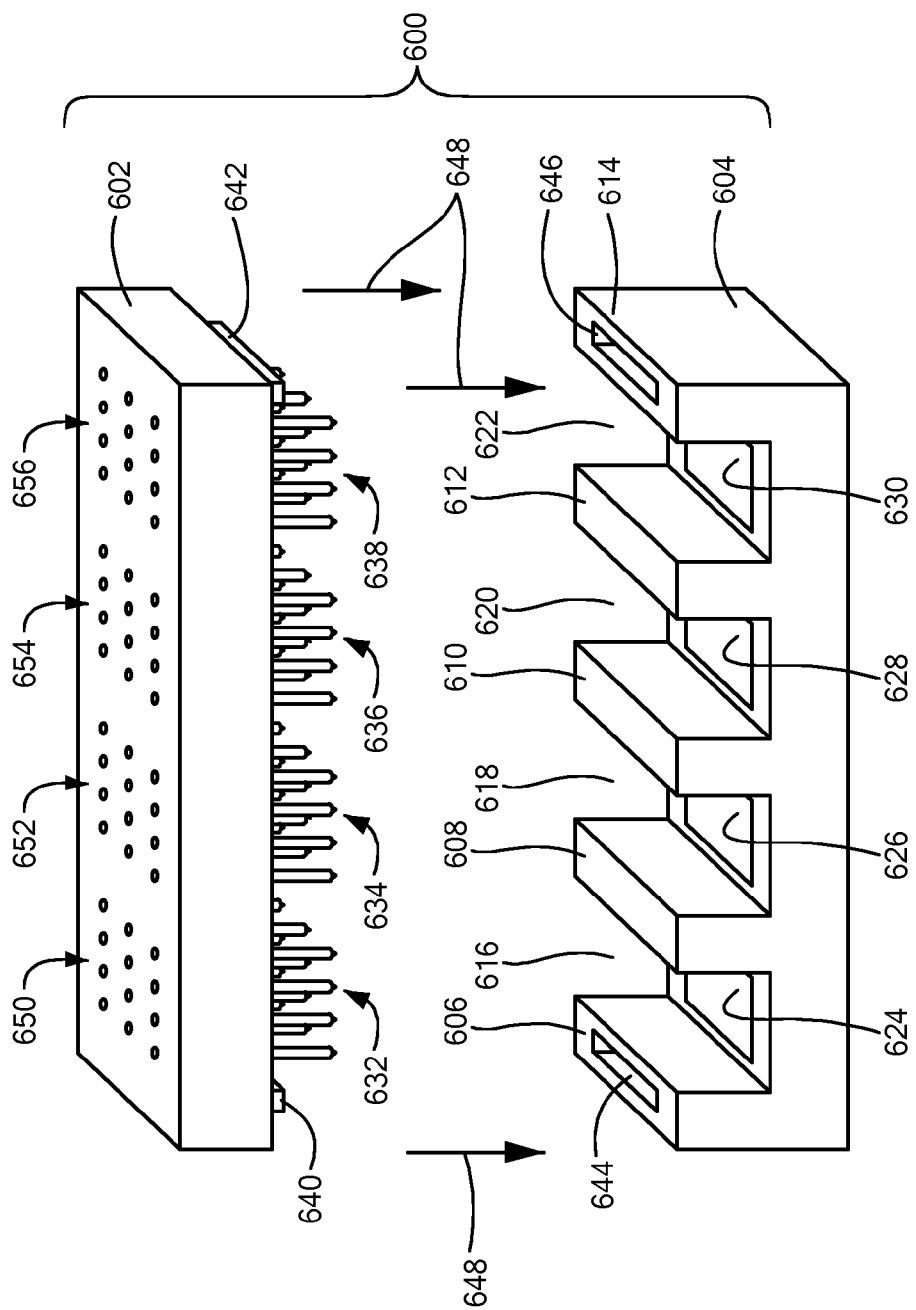
FIG. 6 is a schematic perspective view of a nerve electrode array, according to an embodiment of the present invention.

FIG. 6 is a schematic perspective view of a nerve electrode array 600, according to an embodiment of the present invention. The array 600 includes a lid 602 and a base 604 made of a biocompatible dielectric material, such as polydimethylsiloxane (PDMS). As used herein, a dielectric material is a material having an electrical conductivity no greater than about $10^{-6}$ Ω-m. The base 604 includes a plurality of walls, exemplified by walls 606, 608, 610, 612 and 614. The walls 606-614 define a plurality of horizontally distributed, trench-shaped micro-channels 616, 618, 620 and 622 between adjacent pairs of the walls 606-614. In some embodiments, each micro-channel 616-622 is about 5-5,000 μm wide and about 5-5,000 μm deep. The micro-channels 616-622 may be sized in accordance with sizes of fascicles that are to be placed into the micro-channels 616-622. In some embodiments, each micro-channel 616-622 is at most about 25 cm wide and at most about 25 cm deep. In some embodiments, each micro-channel 616-622 is at most about 25,000 μm wide and at most about 25,000 μm deep. In some embodiments, each micro-channel 616-622 is at most about 5,000 μm wide and at most about 5,000 μm deep. In some embodiments, each micro-channel 616-622 is at most about 500 μm wide and at most about 500 μm deep. In some embodiments, each micro-channel 616-622 is at most about 250 μm wide and at most about 250 μm deep. In some embodiments, each micro-channel 616-622 is at most about 100 μm wide and at most about 100 μm deep. In some embodiments, each micro-channel 616-622 is at most about 50 μm wide and at most about 50 μm deep. In some embodiments, each micro-channel 616-622 is at most about 20 μm wide and at most about 20 μm deep. In some embodiments, each micro-channel 616-622 is at most about 5 μm wide and at most about 5 μm deep. In other embodiments, the micro-channels 616-622 may have other (larger or smaller) widths and/or depths. Each micro-channel 616-622 can be any convenient length.

Each micro-channel includes a reference electrode, exemplified by reference electrodes 624, 626, 628 and 630. Only five walls 606-614 and four micro-channels 616-622 are shown for simplicity. However, an embodiment may include any number of walls and micro-channels. For example, an embodiment intended to interface with a peripheral nerve in a human arm may define on the order of tens or hundreds of micro-channels.

In the embodiment shown in FIG. 6, the lid 602 contains a plurality of micro-wire electrodes, exemplified by electrode sets 632, 634, 636 and 638, extending down from a bottom surface of the lid 602. For simplicity, FIG. 6 shows only 12 micro-wire electrodes in each set of electrodes 632-638. However, any number of electrodes may be included in each set of electrodes 632-638. For example, an embodiment intended to interface with a peripheral nerve in a human arm may include on the order of tens or hundreds of micro-wire electrodes in each set of electrodes 632-638. All the electrode sets 632-638 need not have identical numbers of electrodes. All the electrodes in a given set of electrodes 632-638 can, but need not, be of equal length. The electrodes of each electrode set 632-638 may be arranged in a two-dimensional array and/or along one or more diagonal (with respect to walls 606-614) lines. That is, for each nerve micro-channel 616-622, the micro-wire electrodes 632-638 may be arranged along at least one diagonal line, relative to a longitudinal axis of the respective trench. The longitudinal axis of the trench is parallel to the walls 606-614.

In some embodiments, the electrodes of each electrode set are arranged to have a distance between adjacent electrodes of less than about 125 µm or less than about 100 µm or less than about 40 or less than about 20 µm.

The lid 602 may include tabs 640 and 642 that register with holes 644 and 646 in the outer walls 606 and 614 of the base 604. The lid 602 is configured to be lowered, as indicated by arrows 648, onto the base 604 and mate with the base 604. When the lid 602 mates with the base 604, the tabs 640 and 642 enter the holes 644 and 646, respectively, and the lid closes the micro-channels (trenches) 616-622, defining a nerve capture volume within each micro-channel (trench) 616-622. The lid 602 is associated with the one or more micro-channels (trenches) 616-622. Optionally, each micro-channel (trench) 616-622 has its own associated lid. The electrodes 632-638 are configured and placed on the lid 602 such that, when the lid 602 mates with the base 604, the electrodes 632-638 extend into the micro-channels 616-622. In some embodiments, the electrodes 632-638 protrude at most about 450 µm from the bottom of the lid 602.

Once the lid 602 mates with the base 604, the lid 602 may be secured to the base 604 by any suitable means, such as a releasable or permanent latch, an adhesive or a binding member (not shown) wrapped tightly around the array 600. Optionally, the tabs 640 and 642 may interference fit into the holes 644 and 646, respectively, to partially or completely secure the lid 602 to the base 604. Optionally, the other walls 608, 610 and 612 may define holes (not shown), and the lid 602 may include corresponding tabs (not shown) that fit into the holes when the lid 602 mates with the base 604.

Figure 7:
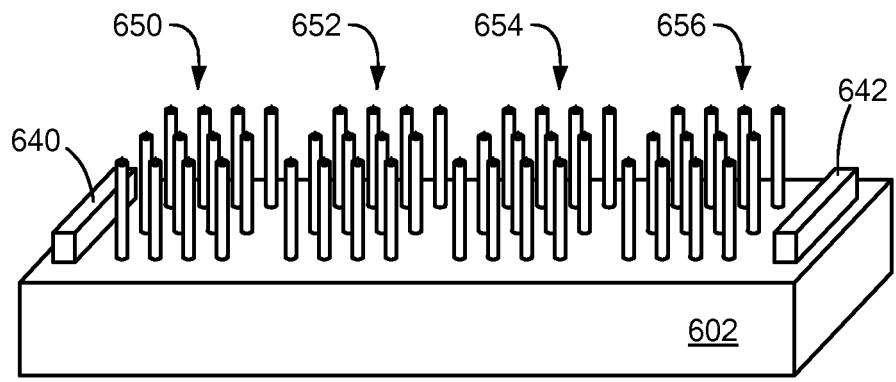
FIG. 7 is a schematic perspective view of a lid of the electrode array in FIG. 6; however, in FIG. 7, the lid is shown up-side-down, relative to its orientation in FIG. 6.

FIG. 7 is a schematic perspective view of the lid 602. However, in FIG. 7, the lid 602 is shown up-side-down, relative to its orientation in FIG. 6. As shown in FIG. 6, in some embodiments, the micro-wire electrodes 632-638 extend through the thickness of the lid 602 to provide electrical connection points, exemplified by electrical connection point sets 650, 652, 654 and 656, on the top surface of the lid 602. FIG. 8 is a schematic cross-sectional view (enlarged, relative to FIGS. 6 and 7, but not to scale) of a portion of the lid 602 and one micro-wire electrode 800. The micro-wire electrode 800 may be attached to the lid 602 in any suitable manner. For example, the electrode 800 may be driven through the lid 602 and held in place by friction between the lid 602 and the electrode 800. Optionally or alternatively, the micro-wire electrode 800 may be attached to the lid via a chemical modification. For example, in embodiments in which the micro-wire electrode 800 is made of silicon, or at least has a silicon outer sheath, the micro-wire electrode 800 may be covalently attached to the lid 602, such as by oxygen plasma bonding. If the micro-wire electrode 800 is made of gold, thiol chemistry may be used to attach the micro-wire electrode 800 to the lid 602.

In one embodiment, the micro-wire electrode 800 includes an electrically conductive core 802 having a diameter 803 of about 4 µm. As used herein, electrically conductive means having an electrical resistance less than about 10 MΩ. The resistance may depend on material and cross-sectional area of the electrode. Resistances above about 5 MΩ may require suitable amplifiers. Typical metallic cores 802 may have resistances of about 200 kΩ to about 600 kΩ, although higher or lower resistances are acceptable. Carbon-based electrodes, discussed herein, typically have higher resistances, typically greater than about 1 MΩ, than metallic electrodes. Similarly, conductive polymer-based electrodes, discussed herein, may have higher resistances than metallic electrodes.

In some embodiments, the core 802 is made of metal. The core 802 is sharpened to a point 804. Optionally, the point 804 may be coated (not shown) with a biocompatible, electrically conductive material, such as gold. The core 802 is electrically insulated, at least along its expose length 805 (except for the point portion 804) by an electrically insulating layer 806, such as an about 5-6 µm thick 807 layer of glass. As used herein, electrically insulated and electrically non-conductive mean having an electrical resistance of at least about $10^{-6}$ Ω-m. In this configuration, the micro-wire has an outside diameter 808 of about 14-16 µm. In some embodiments, the outside diameter 808 is at most about 25 µm substantially along its protrusion length 805 from the lid 602. In other words, the protruding portion is not tapered. In some embodiments, the uninsulated point portion 804 is at most about 10 µm long, as indicated by 809. Suitable micro-wire electrodes 800 are available from RED Micro Wire, 2 Woodlands Sector 1, #01-18, Singapore 738068.

Optionally or alternatively, micro-wire electrodes may be made from bulk micro-wire. For example, bulk micro-wire having a diameter of about 8-10 µm, or other desirable diameter, may be cut into suitable length pieces, and the pieces may be laid in complementarily-sized grooves in a silicon chip, and chip assemblies may be placed inside the respective micro-channels 616-622. Suitable bulk micro-wire is available from RED Micro Wire.

Alternatively, the micro-wire electrode 800 may be made of a carbon fiber core, with a suitable thin film coating dielectric (except at its tip). Such a micro-wire electrode may have a diameter, including the dielectric layer, of about 8 µm. The uninsulated tip of the micro-wire electrode can, but need not, be pointed. However, the tip should be coated with an electrically conductive polymer, such as poly(3,4-ethylenedioxythiophene):poly(4-styrenesulfonate) (PEDOT:PSS), or another suitable electrically conductive material. Such a carbon fiber core-based electrode is described by Takashi D. Yoshida Kozai, et al. in "Ultrasmall implantable composite microelectrodes with bioactive surfaces for chronic neural interfaces," published online in Nature Materials, Vol. 11, on Nov. 11, 2012 by Macmillan Publishers Limited, the entire contents of which are hereby incorporated herein. However, Kozai's microelectrodes were implanted directly in brain tissue, without use of micro-channels as described herein.

Individual micro-wire electrodes are preferable to silicon-based three-dimensional electrode arrays fabricated using photolithographic processes, such as the well-known Utah electrode array, because individual micro-wire electrodes are smaller in diameter and relatively uniform in diameter along their lengths. In contrast, Utah electrodes taper from a sharp point to a relatively large cross-sectional size at their bases. As used herein, the term "micro-wire" refers to an individual electrode, not part of an array of electrodes that are all fabricated as a solid unit, as the Utah electrode array is fabricated.

Figure 9:
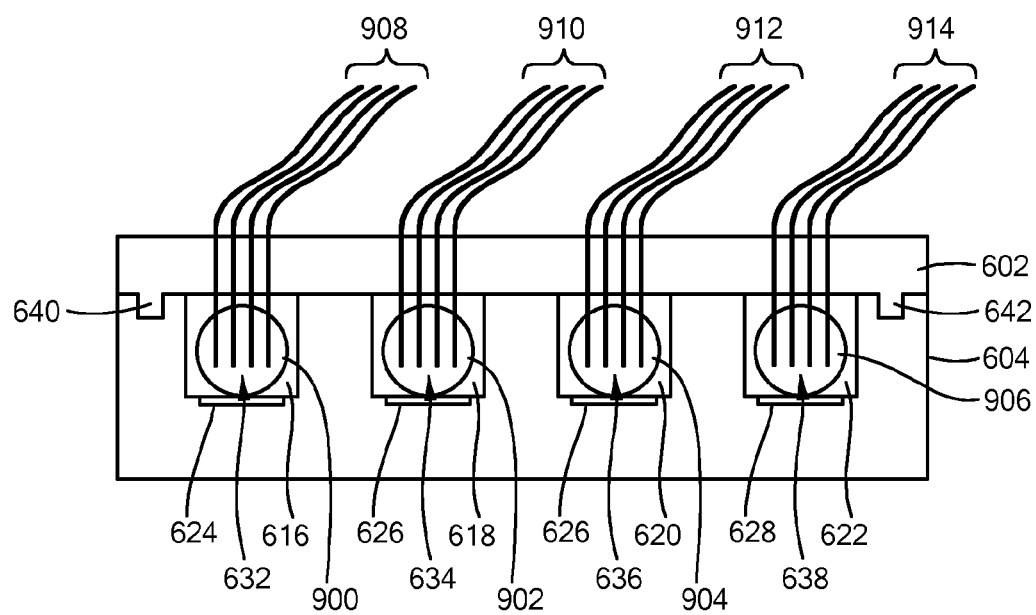
FIG. 9 is a schematic cross-sectional view of the electrode array of FIG. 6, with fascicles disposed in the micro-channels of the electrode array.
Figure 10:
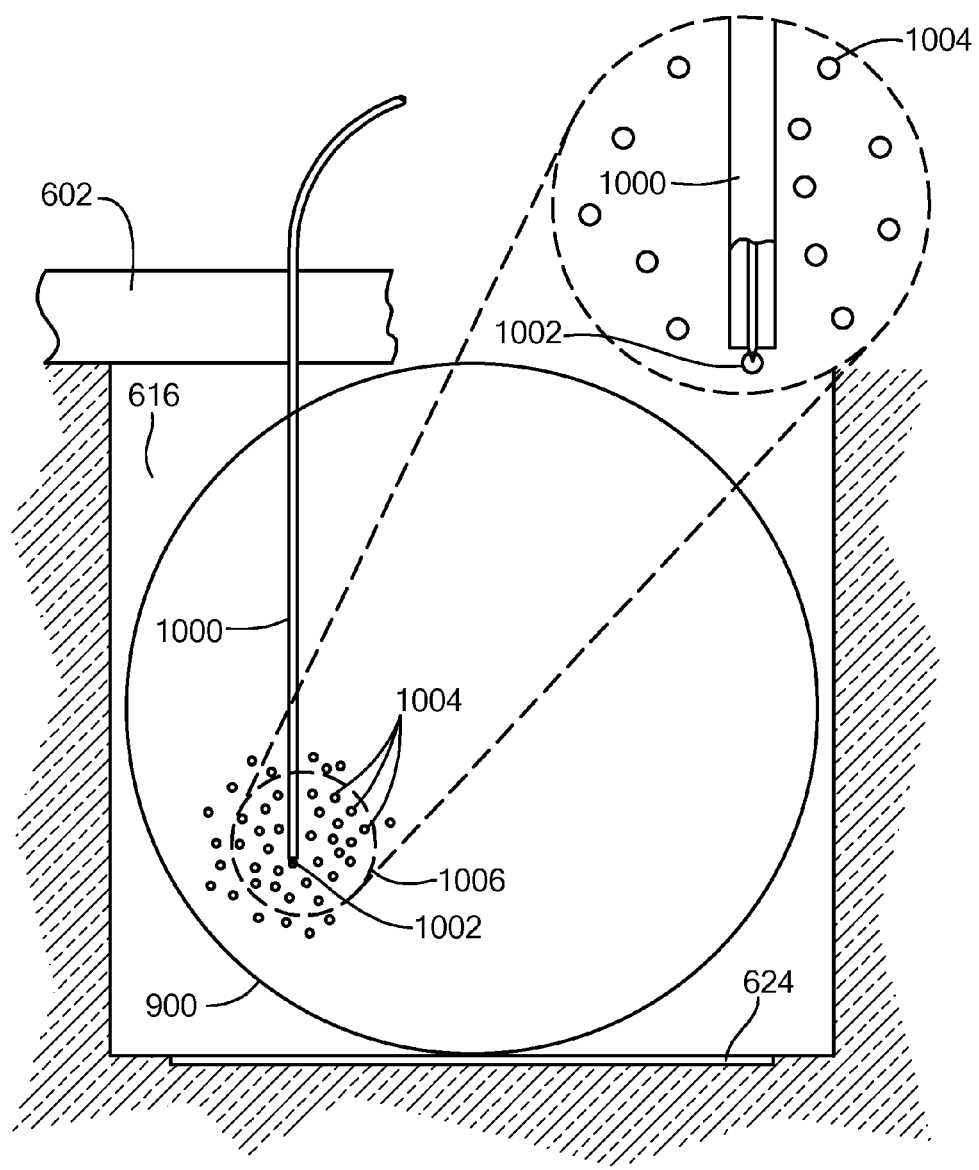
FIG. 10 is an enlarged schematic view of a portion of the micro-channel of FIG. 9.

Returning to FIG. 8, a wire 810 may be electrically and mechanically connected to the conductive core 802, such as via a weld 812. In use, a separate fascicle 900, 902, 904 and 906 is placed in each micro-channel 616-622, and the lid 602 is attached to the base 604, as shown schematically in cross-sectional view in FIG. 9. As the lid 602 is attached to the base 604, the micro-wire electrodes 632-638 penetrate the fascicles 900-906, making electrical contact with axons in the fascicles 900-906. FIG. 10 is an enlarged schematic view of a portion of the micro-channel 616 of FIG. 9. For simplicity, only one micro-wire electrode 1000 is shown in FIG. 10. The micro-wire electrode 1000 is shown having penetrated the fascicle 900 and having made electrical contact with an axon 1002 within the fascicle 900. Other axons, exemplified by axons 1004, in the vicinity of the tip of the micro-wire electrode 1000 are also shown. A portion of FIG. 10 enclosed in dashed circle 1006 is shown enlarged in the upper-right corner of FIG. 10.

Returning to FIG. 9, wires, exemplified by wire sets 908, 910, 912 and 914, provide electrical connections to and from the micro-wire electrodes 632-638. In addition, the reference electrodes 624-630 provide ground (reference) potentials, against which signals on the micro-wire electrodes 632-638 may be referenced. Additional wires (not shown for clarity) extend from the reference electrodes 624-630. The wires electrically connected to the reference electrodes 624-630 and the wire sets 908-914 extending from the micro-wire electrodes 632-638 may be coupled, directly or indirectly, to an appropriate circuit (not shown) to analyze signals in the axons and/or to electrically stimulate the axons.

Figure 11:
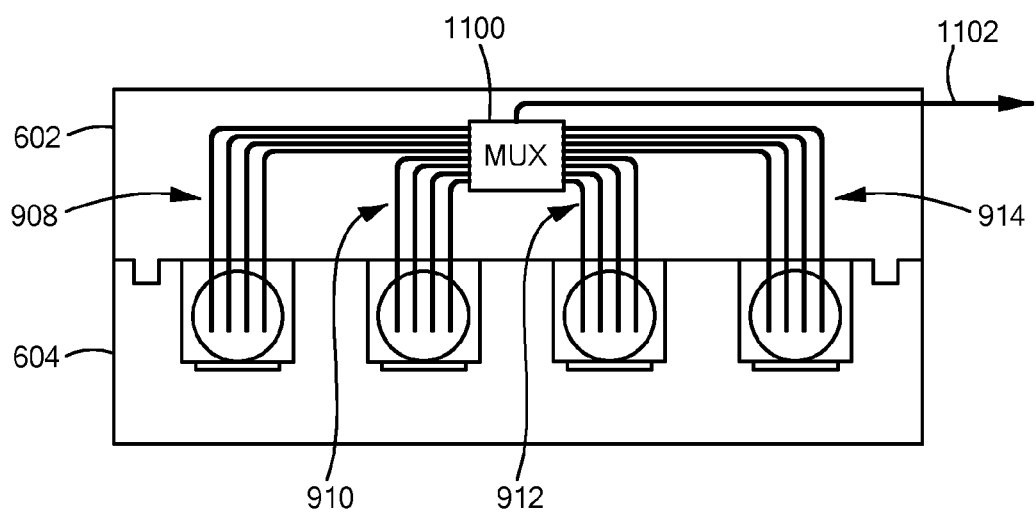
FIG. 11 is a cross-sectional view of an electrode array, similar to the electrode array of FIG. 6, but including a multiplexor, according to another embodiment of the present invention.

Rather than extending a separate wire from each micro-wire electrode 632-638 to the analysis/signal generating circuit, a multiplexer (MUX) 1100 may be included in the lid 602, as shown schematically in FIG. 11. In this case, the wire sets 908-914 may terminate at the MUX 1100, which multiplexes access to the individual micro-wire electrodes 632-638 via a single wire or small set of wires 1102 extending directly or indirectly to the analysis/signal generating circuit (not shown). Alternatively, rather than wires 908-914, the micro-wire electrodes 632-638 may be formed to extend to, and electrically connect to, the MUX 1100. Although FIG. 11 shows a single MUX 1100, multiple multiplexors may be used, such as separate multiplexors for multiplexing signals from and to the axons.

Figure 12:
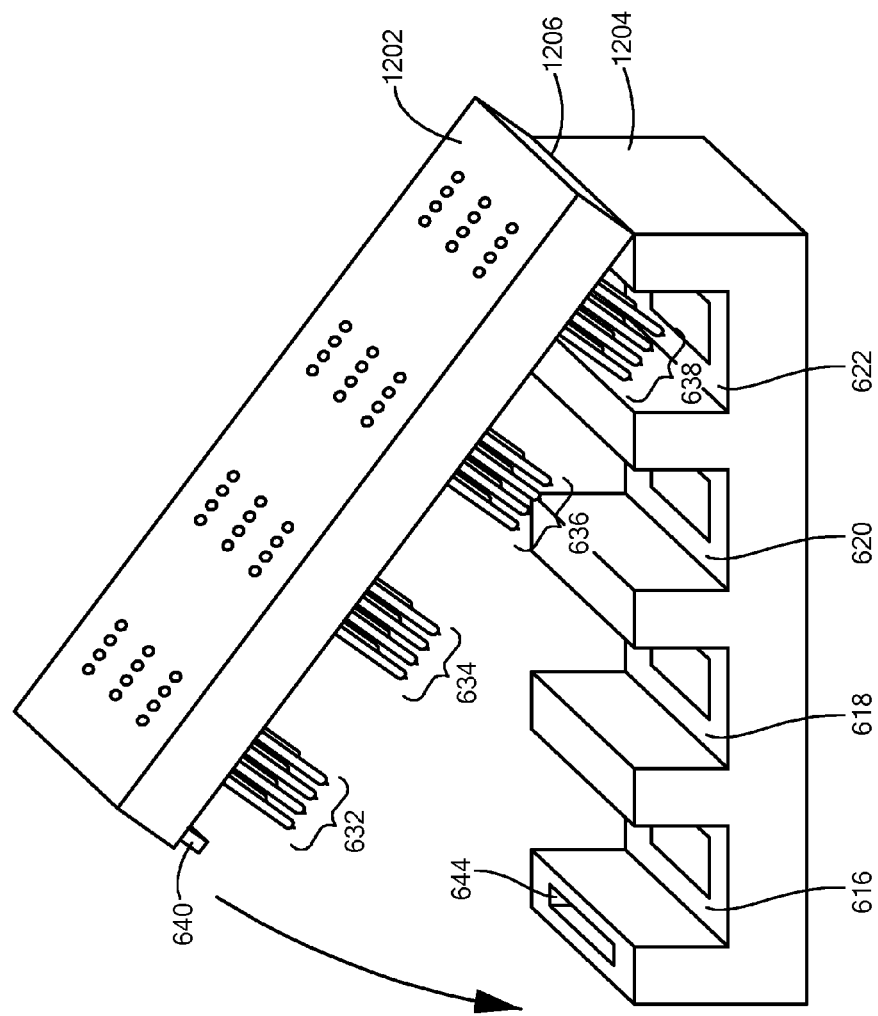
FIG. 12 is a schematic perspective view of a nerve electrode array, according to yet another embodiment of the present invention.

The embodiments discussed above, with respect to FIGS. 6, 7, 9, 10 and 11, include a lid 602 that is lowered onto, and attaches to, a base 604. Alternatively, as shown schematically in FIG. 12, a lid 1202 may be hingedly attached to a base 1204, such as by a living hinge 1206. Other aspects of the embodiment shown in FIG. 12 are similar to those described elsewhere herein.

Figure 13:
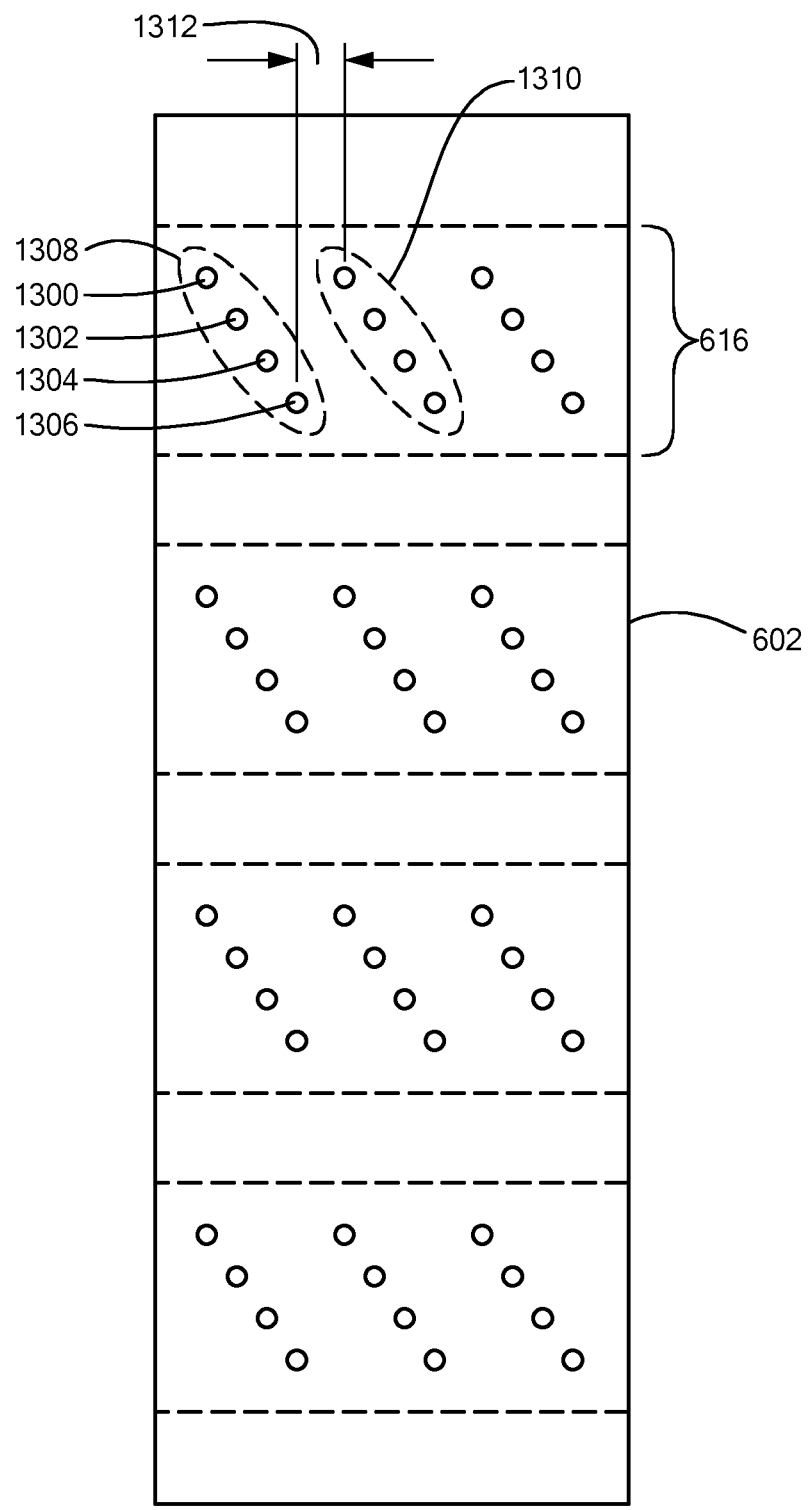
FIG. 13 is a schematic top view of the lid of the electrode array of FIG. 6, in which the micro-wire electrodes are arranged in a staggered fashion, according to another embodiment of the present invention.
Figure 14:
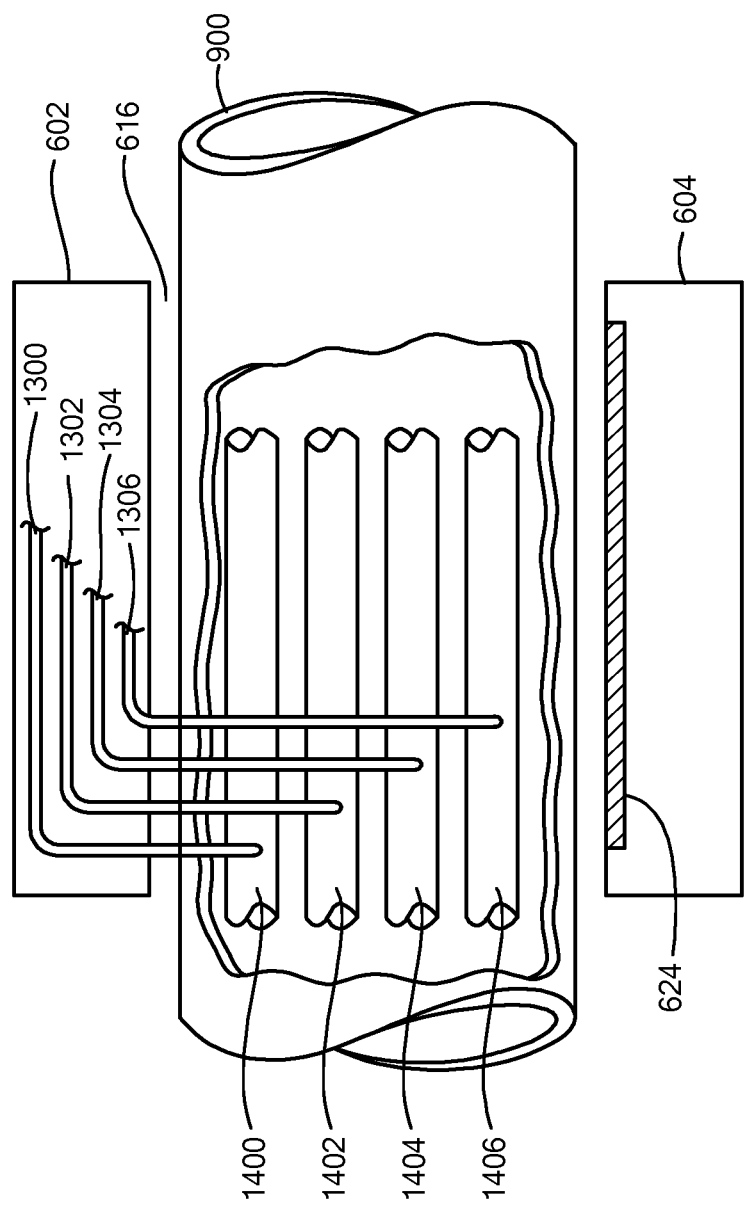
FIG. 14 is a schematic cross-sectional view of the lid, base, fascicle and several micro-wire electrodes of FIG. 13.

As shown in FIG. 6, the micro-wire electrodes 632-638 of each set of micro-wire electrodes may be arranged in a rectangular array. However, other arrangements are possible. FIG. 13 is a schematic top view of the lid 602, in which the micro-wire electrodes, exemplified by micro-wire electrodes 1300, 1302, 1304 and 1306, which are associated with one of the micro-channels 616, are arranged in a staggered fashion. Dashed lines indicate sides of the walls 606-614 (FIG. 6). Such staggering may be advantageous, particularly when fascicle diameter is less than inter-electrode spacing. Although three groups of micro-wire electrodes are shown in FIG. 13 (each group aligned along a diagonal), other numbers of groups, such as one group, two groups or more than three groups, may be used. FIG. 14 is a schematic cross-sectional view of the lid 602, base 604, fascicle 900 in the micro-channel 616 and several micro-wire electrodes 1300-1306 of FIG. 13.

As shown in FIG. 14, the micro-wire electrodes 1300-1306 may extend to different depths, so as to make contact with axons, exemplified by axons 1400, 1402, 1404 and 1406, at corresponding depths within the fascicle 900. In some embodiments, at least one micro-wire electrode 1300-1306 protrudes at most about 125 μm, but less than about 250 μm, and another at least one micro-wire electrode 1300-1306 protrudes at least about 275 μm, from the lid 602. In some embodiments, groups of the micro-wire electrodes, exemplified by groups 1308 and 1310, are spaced longitudinally along each micro-channel, such that electrodes of two adjacent groups are spaced apart 1312 from each other by at most about 100 μm or at most about 125 μm.

Figure 15:
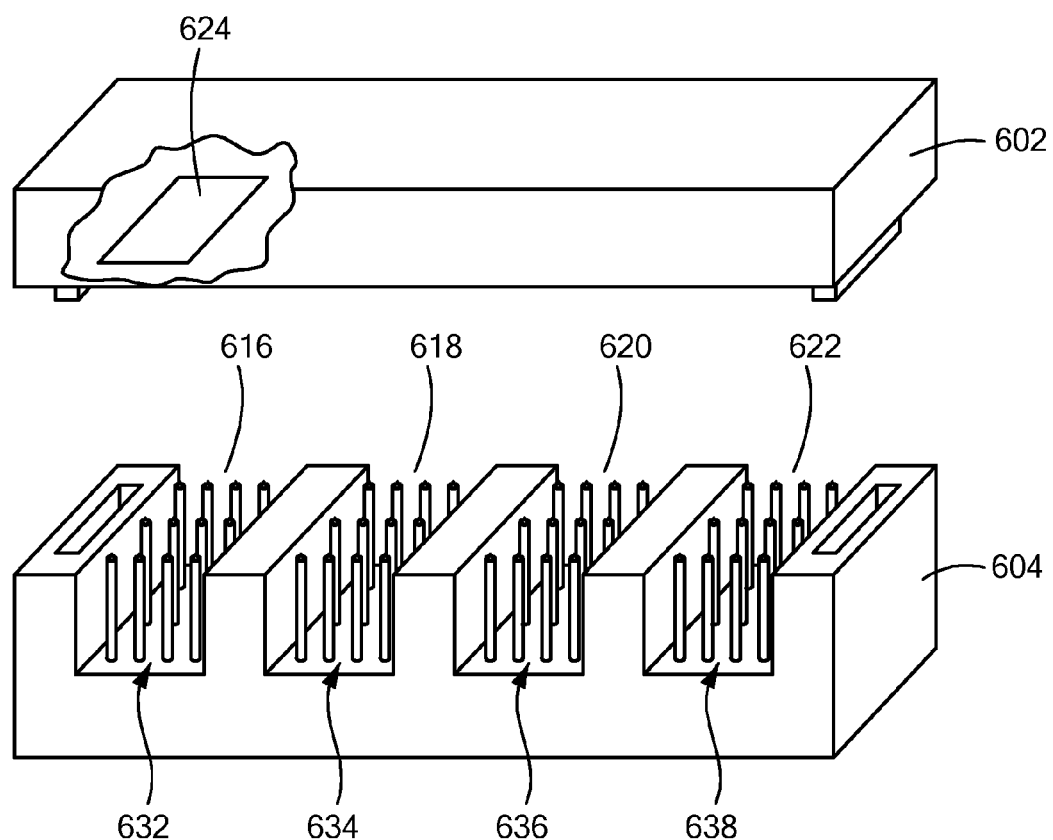
FIG. 15 is a schematic perspective view of a nerve electrode array, according to yet another embodiment of the present invention.

Embodiments having micro-wire electrodes 632-638 extending down from the lid 602 have been described. However, as noted, the micro-wire electrodes 632-638, or at least some of the micro-wire electrodes 632-638, may extend up from the bottom of the micro-channels 616-622, as schematically shown in FIG. 15. In this case, the bottom of the lid 602 may include the reference electrodes 624-630. In some embodiments, some micro-wire electrodes extend down from a lid, and other micro-wire electrodes extend up from a bottom of micro-channels. These embodiments may include reference electrodes in the lid and/or in the bottom of the micro-channels.

Figure 16:
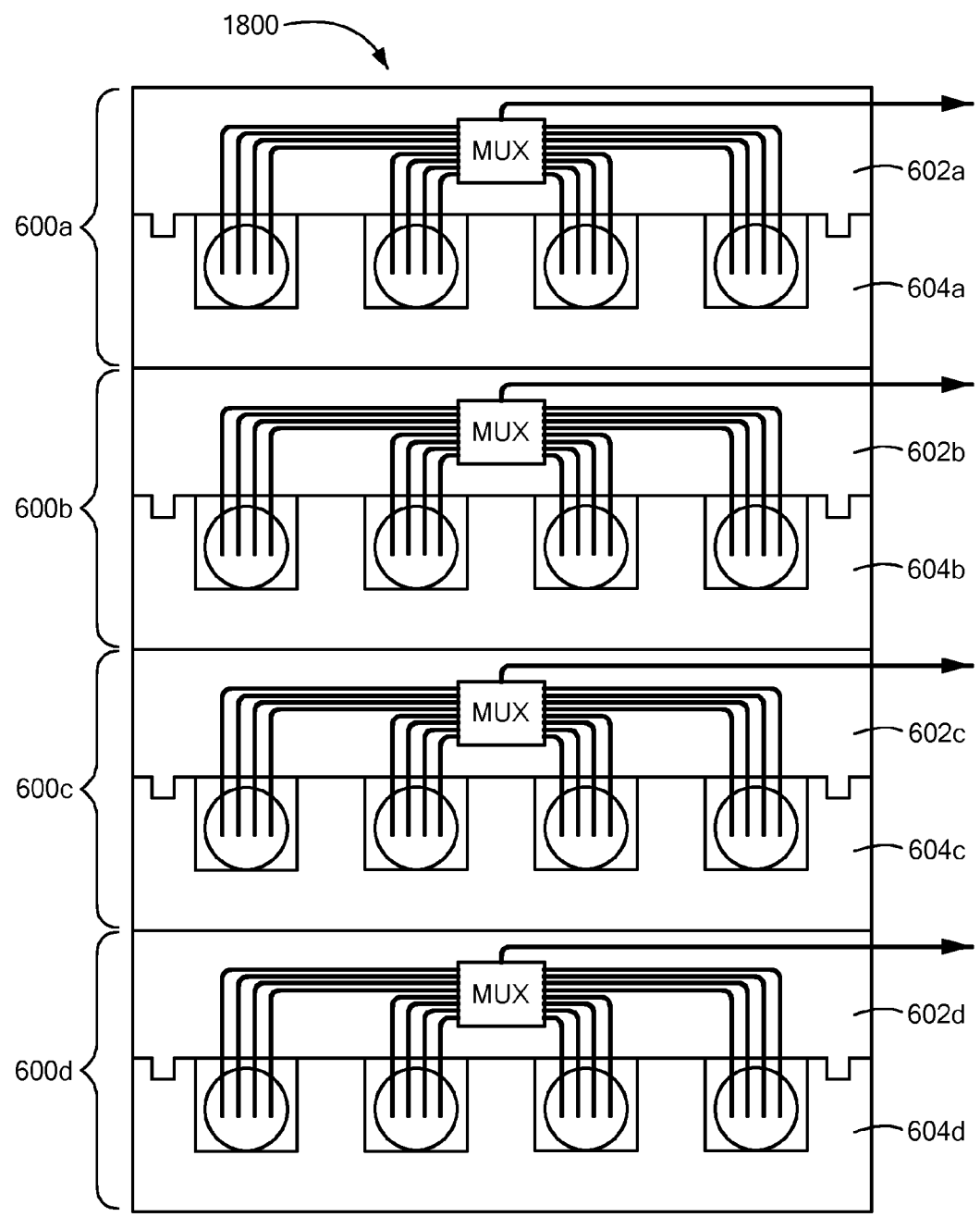
FIG. 16 is a schematic cross-sectional view of several rows of electrode arrays arranged in a two-dimensional fashion, according to another embodiment of the present invention.

Several electrode arrays, exemplified by electrode arrays 600a, 600b, 600c and 600d, may be stacked to create a two-dimensional (as viewed from its face) electrode array 1600 having a plurality of vertically distributed rows of micro-channels, as schematically illustrated in FIG. 16. The base 604a of one electrode array 600a may be integral with the lid 602b of its adjacent electrode array 600b, or the bases 604a-604c may be separate from their adjacent lids 602b-602d. In the latter case, the electrode arrays 600a-d may be attached to their respective neighbors in any suitable manner, as discussed above, with respect FIG. 6, in reference to attaching the lid 602 to the base 604. Although four electrode arrays 600a-d are shown joined together in FIG. 16, other numbers of electrode arrays may be joined together.

Figure 17:
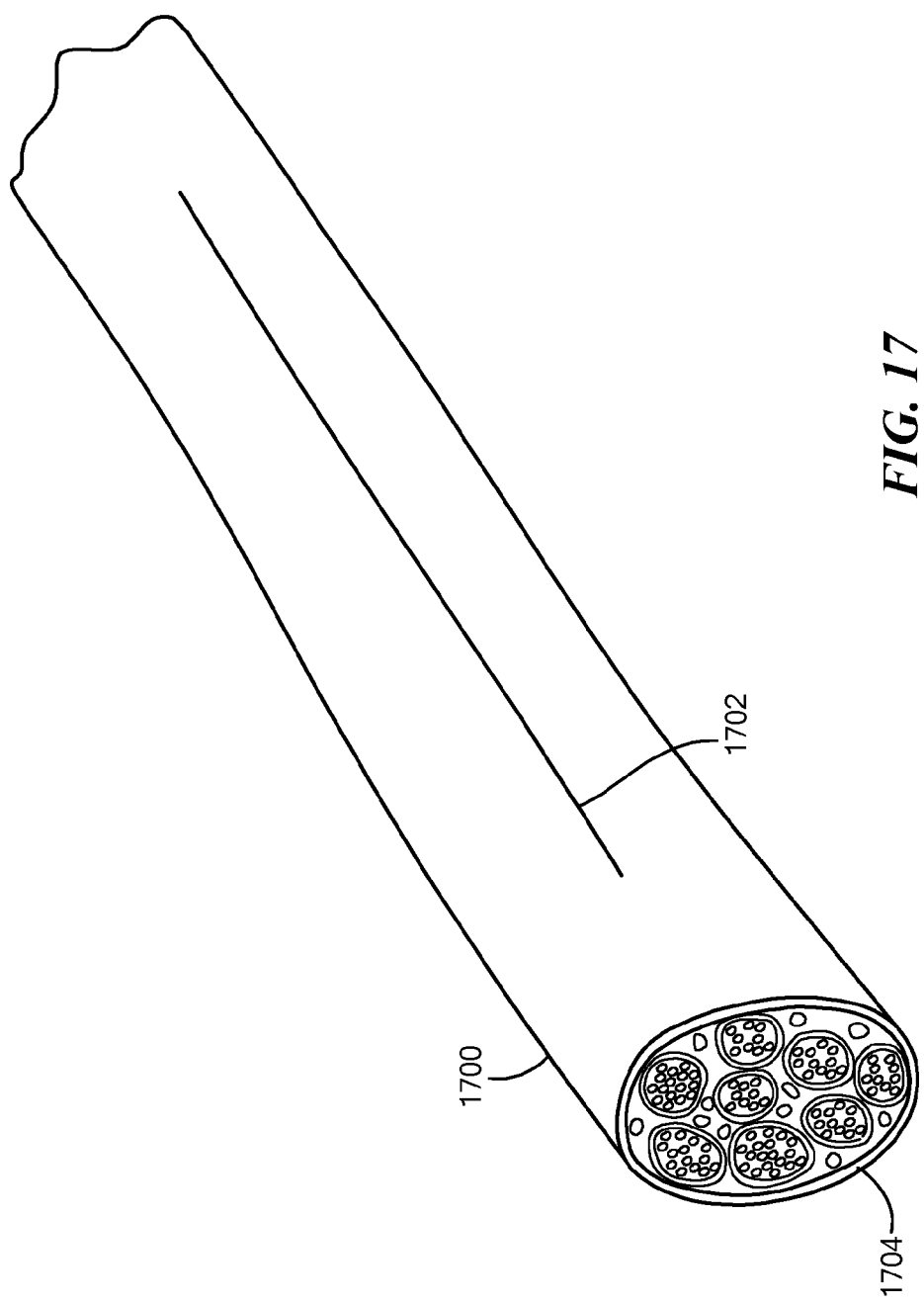
FIGS. 17-20 schematically illustrate a sequence of operations, by which fascicles of a nerve may be connected to an electrode array, without severing the nerve into two disconnected portions, according to an embodiment of the present invention.
Figure 18:
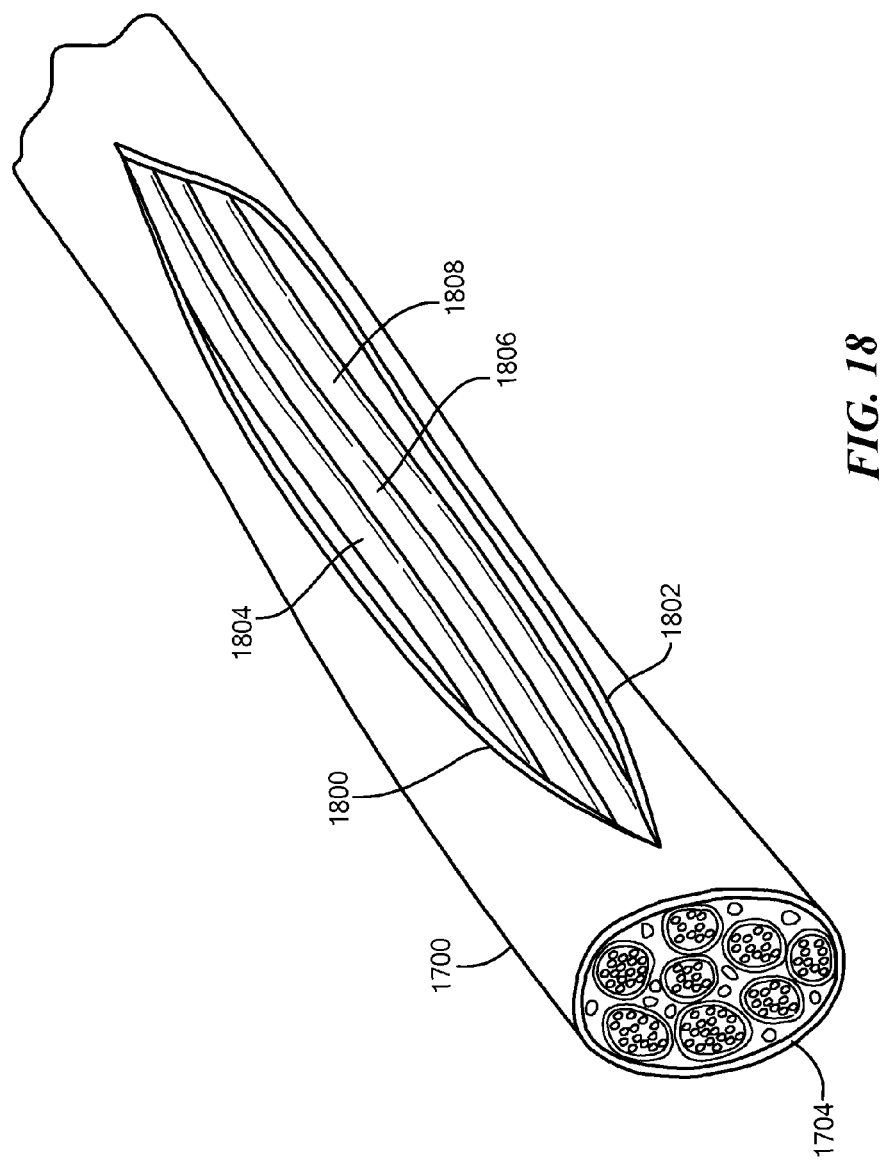

FIGS. 17-20 schematically illustrate a sequence of operations, by which fascicles of a nerve 1700 may be connected to an electrode array, without severing the nerve 1700 into two disconnected portions, as would be necessary when using a prior art jelly-roll nerve electrode array (FIGS. 2-5). In FIG. 17, a longitudinal incision 1702 is made in the epineurial sheath 1704 of the nerve 1700, thereby creating two lips 1800 and 1802 of epineurial sheath 1704, and exposing fascicles, exemplified by fascicles 1804, 1806 and 1808, as shown in FIG. 18.

Figure 19:
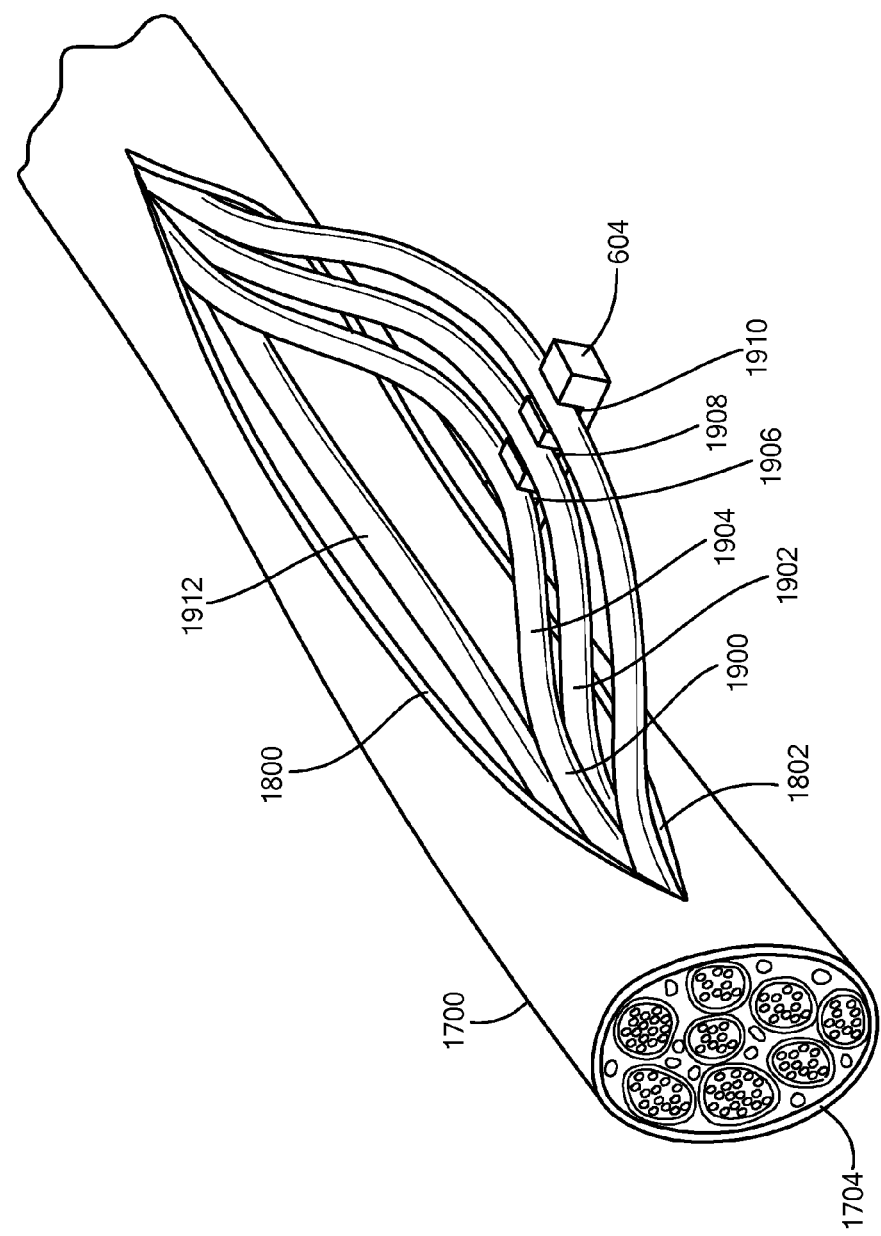

As shown in FIG. 19, fascicles of interest, exemplified by fascicles 1900, 1902 and 1904, may be extended, between the lips 1800 and 1802, from the nerve 1700, and placed in respective micro-channels, exemplified by micro-channels 1906, 1908 and 1910, of the base 604 of an electrode array. The fascicles 1900-1904 that are extended from the nerve 1700 and placed in the micro-channels 1906-1910 may be a subset of, or all of, the fascicles in the nerve 1700. In FIG. 19, one fascicle 1912 is shown not placed in any micro-channel of the base 604.

Figure 20:
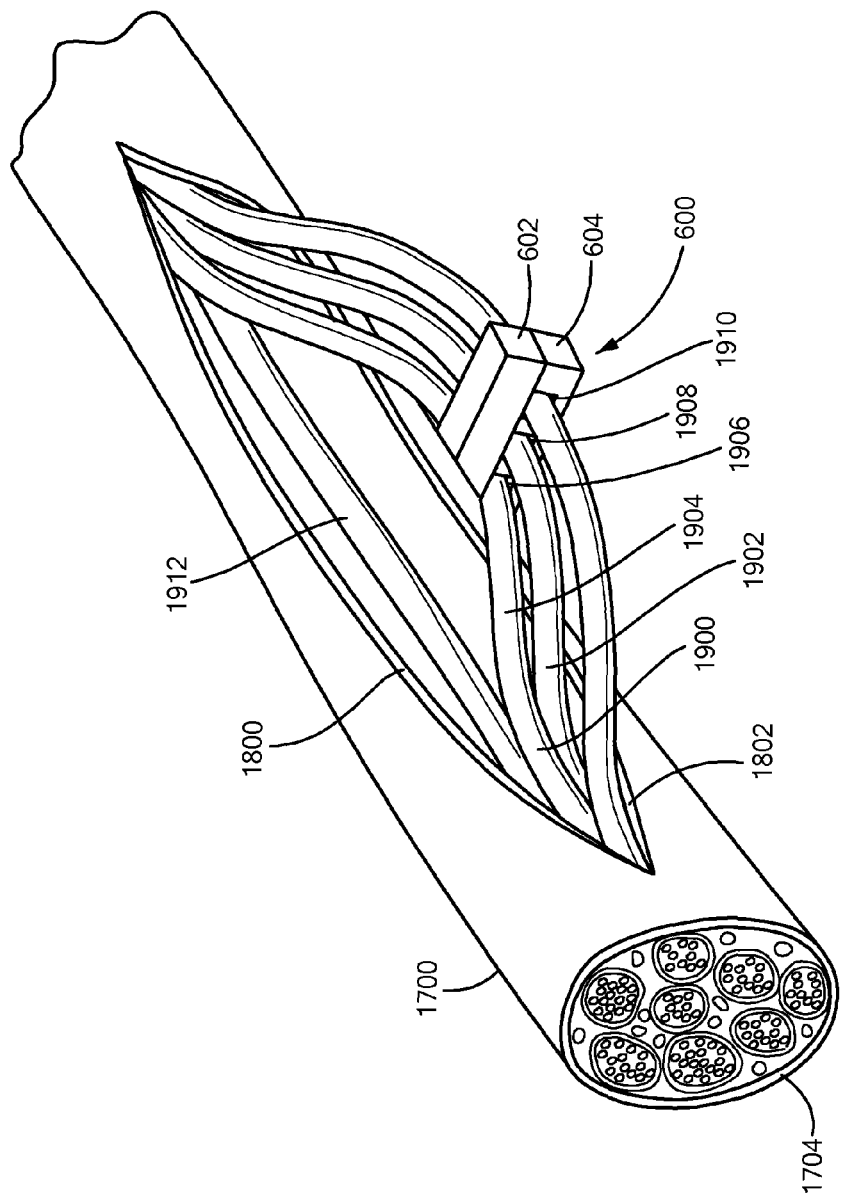

As shown in FIG. 20, once the fascicles of interest have been placed in the respective micro-channels, the lid 602 is attached to the base 604. The micro-wire electrodes (not visible) of the electrode array 600 penetrate the fascicles 1900-1904 and make electrical contact with respective axons (not visible) in the fascicles 1900-1904, as described herein. An electrode array 600 having only one row of micro-channels is shown. However, as discussed herein, the electrode array 600 may include a plurality of rows of micro-channels.

Figure 21A:
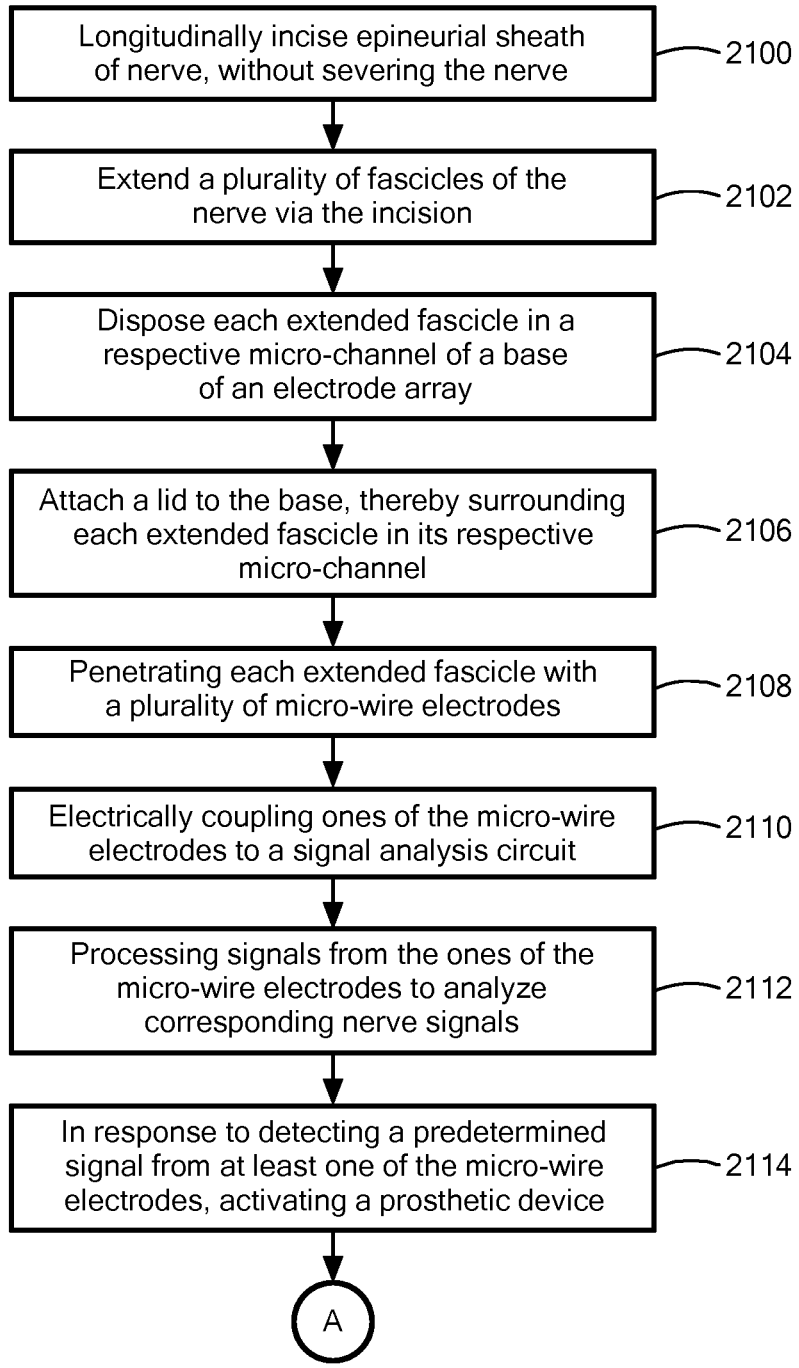
FIGS. 21 (A and B) contains a flowchart schematically illustrating a process for attaching electrodes to portions of a nerve, according to an embodiment of the present invention.
Figure 21B:
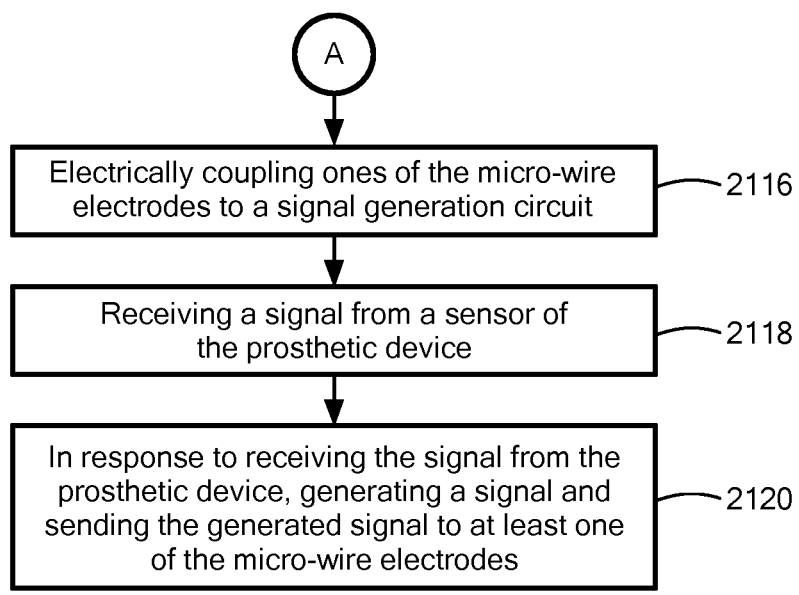

FIGS. 21 (A and B) contains a flowchart schematically illustrating a process for attaching electrodes to portions of a nerve. Some of the operations of the process may be performed as shown in FIGS. 17-20. At 2100, the nerve is longitudinally incised, without severing the nerve into two pieces. At 2102, a plurality of fascicles of the nerve is extended via the incision in the nerve. At 2104, each extended fascicle is disposed in a respective micro-channel of a base of an electrode array. At 2106, a lid is attached to the base, thereby surrounding each extended fascicle in its respective micro-channel. The base and the lid collectively surround the fascicle.

At 2108, each fascicle is penetrated with a plurality of micro-wire electrodes. Each micro-wire electrode may be less than about 15-17 µm in diameter, including any insulation on the micro-wire. Each fascicle is penetrated by at least about 3-15 micro-wire electrodes (for example, in the case of a sciatic nerve). At 2110, at least some of the micro-wire electrodes are electrically coupled to a signal analysis circuit. At 2112, signals from the at least some of the micro-wire electrodes are processed to analyze corresponding nerve signals. At 2114, in response to detecting a predetermined signal from at least one of the micro-wire electrodes, a prosthetic device is activated. For example, a motor may be activated to move a prosthetic digit or appendage of the prosthetic device.

At 2116, at least some other of the micro-wire electrodes are electrically coupled to a signal generation circuit. At 2118, a signal is received from a sensor, such as a touch, heat, moisture or pressure sensor, of the prosthetic device. At 2120, in response to receiving the signal from the prosthetic device sensor, a signal is generated by the signal generation circuit, and the generated signal is sent to at least one of the micro-wire electrodes, thereby stimulating a corresponding portion of the nerve.

Various dimensions and numbers of rows and micro-channels per row may be used, depending on an intended use of the electrode array.

While the invention is described through the above-described exemplary embodiments, modifications to, and variations of, the illustrated embodiments may be made without departing from the inventive concepts disclosed herein. Furthermore, disclosed aspects, or portions thereof, may be combined in ways not listed above and/or not explicitly claimed. Accordingly, the invention should not be viewed as being limited to the disclosed embodiments.

What is claimed is:

1. A method for fabricating an electrode array, the method comprising:
    forming a bio-compatible dielectric substrate;
    defining a plurality of parallel trenches in the substrate, each trench of the plurality of trenches having a longitudinal axis, an open top extending parallel to the longitudinal axis and a bottom and two parallel sides defined by the substrate and extending parallel to the longitudinal axis, each trench being at most 5 mm wide and at most 5 mm deep;
    forming a bio-compatible dielectric lid having a top surface and an opposite bottom surface, the lid being attachable via the bottom surface to the substrate, such that when the lid is attached to the substrate, the lid covers each trench, such that each trench defines a hollow nerve capture volume bounded by the bottom and the two sides of the trench and by the bottom surface of the lid, the hollow nerve capture volume extending along the longitudinal axis of the trench;
    forming a plurality of electrodes, each electrode of the plurality of electrodes being formed from bulk micro-wire, and each electrode of the plurality of electrodes having an electrically conductive portion at most 4 µm in diameter; and
    driving the plurality of electrodes through the lid such that each electrode extends beyond the bottom surface of the lid, the plurality of electrodes being disposed about the lid such that, when the lid is attached to the substrate, at least ten electrodes of the plurality of electrodes extend into the nerve capture volume of each trench, wherein, prior to driving the plurality of electrodes through the lid, each electrode of the plurality of electrodes is distinct from the lid and distinct from the substrate.

2. A method according to claim 1, further comprising holding each electrode of the plurality of electrodes in place, relative to the lid, using friction between the lid and the electrode.

3. A method according to claim 1, further comprising performing a chemical modification to hold each electrode of the plurality of electrodes in place, relative to the lid.

4. A method according to claim 3, wherein performing the chemical modification comprises covalently bonding at least an outer sheath of each electrode of the plurality of electrodes to the lid.

5. A method according to claim 4, wherein covalently bonding comprises oxygen plasma bonding.

6. A method according to claim 3, wherein performing the chemical modification comprises using thiol chemistry.

7. A method for fabricating an electrode array, the method comprising:
    forming a bio-compatible dielectric substrate;
    defining a plurality of parallel trenches in the substrate, each trench of the plurality of trenches having a longitudinal axis, an open top extending parallel to the longitudinal axis and a bottom and two parallel sides defined by the substrate and extending parallel to the longitudinal axis, each trench being at most 5 mm wide and at most 5 mm deep;
    forming a bio-compatible dielectric lid having a top surface and an opposite bottom surface, the lid being attachable via the bottom surface to the substrate, such that when the lid is attached to the substrate, the lid covers each trench, such that each trench defines a hollow nerve capture volume bounded by the bottom and the two sides of the trench and by the bottom surface of the lid, the hollow nerve capture volume extending along the longitudinal axis of the trench;
    forming a plurality of electrodes, each electrode of the plurality of electrodes being formed from bulk micro-wire, and each electrode of the plurality of electrodes having an electrically conductive portion at most 4 µm in diameter;

driving the plurality of electrodes through the lid such that each electrode extends beyond the bottom surface of the lid, the plurality of electrodes being disposed about the lid such that, when the lid is attached to the substrate, at least ten electrodes of the plurality of electrodes extend into the nerve capture volume of each trench; and holding each electrode of the plurality of electrodes in place, relative to the lid, using friction between the lid and the electrode.

8. A method according to claim 7, wherein, prior to driving the plurality of electrodes through the lid, each electrode of the plurality of electrodes is distinct from the lid and distinct from the substrate.

9. A method according to claim 7, further comprising performing a chemical modification to hold each electrode of the plurality of electrodes in place, relative to the lid.

10. A method according to claim 9, wherein performing the chemical modification comprises covalently bonding at least an outer sheath of each electrode of the plurality of electrodes to the lid.

11. A method according to claim 10, wherein covalently bonding comprises oxygen plasma bonding.

12. A method according to claim 9, wherein performing the chemical modification comprises using thiol chemistry.

\* \* \* \* \*